United States Patent
Odabashian et al.

(10) Patent No.: US 12,042,174 B2
(45) Date of Patent: Jul. 23, 2024

(54) CANNULA FOR GRASPING AND SETTING LEAD WITH NEEDLE

(71) Applicant: Neuralink Corp., Fremont, CA (US)

(72) Inventors: Christine M. Odabashian, Los Gatos, CA (US); Ian M. O'Hara, San Francisco, CA (US)

(73) Assignee: Neuralink Corp., Fremont, CA (US)

( * ) Notice: Subject to any disclaimer, the term of this patent is extended or adjusted under 35 U.S.C. 154(b) by 364 days.

(21) Appl. No.: 17/711,980

(22) Filed: Apr. 1, 2022

(65) Prior Publication Data

US 2023/0310028 A1 Oct. 5, 2023

(51) Int. Cl.
*A61B 17/34* (2006.01)
*A61B 34/32* (2016.01)

(52) U.S. Cl.
CPC ...... *A61B 17/3468* (2013.01); *A61B 17/3423* (2013.01); *A61B 34/32* (2016.02); *A61B 2017/3425* (2013.01)

(58) Field of Classification Search
CPC . A61B 17/3468; A61B 17/3423; A61B 34/32; A61B 2017/3425; A61B 17/3403; A61B 2017/3409; A61N 1/0534
See application file for complete search history.

(56) References Cited

U.S. PATENT DOCUMENTS

| | | |
|---|---|---|
| 2019/0286592 A1 | 9/2019 | Seo |
| 2020/0085508 A1 | 3/2020 | O'Hara |
| 2020/0086111 A1 | 3/2020 | Young |

OTHER PUBLICATIONS

Kral et al., Prosthesis for the Brain: Introduction to Neuroprosthetics, Academic Press, Apr. 3, 2021, pp. 344-345.

*Primary Examiner* — Richard G Louis
(74) *Attorney, Agent, or Firm* — Kilpatrick Townsend & Stockton LLP

(57) ABSTRACT

Systems and methods are disclosed for a lead, needle, and cannula that are sized and shaped for ease of needle threading and positioning, e.g., for implanting the lead into biological tissue. The lead has an opening at one end surrounded by an expanded region. The needle has a ledge in a side of the needle. The cannula has an exit gate with an aperture sized to accept the expanded region of the lead. A portion of the needle is held inside the cannula and can extend or retract therein. When the expanded region of the lead is threaded through the exit gate aperture, the needle is configured to extend through the opening of the lead and catch the lead on the ledge. The needle is further configured to extend past the exit gate of the cannula while pulling the lead through the slot and free of the aperture.

20 Claims, 15 Drawing Sheets

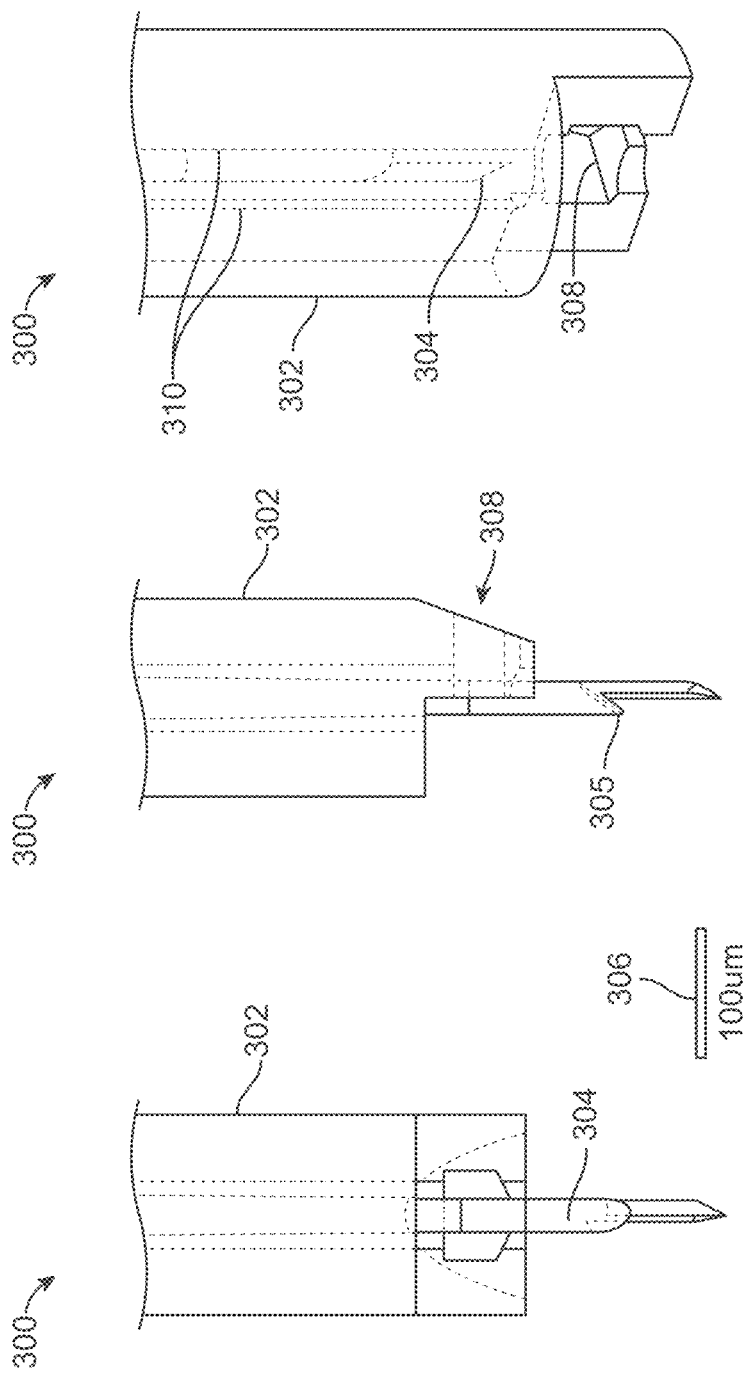

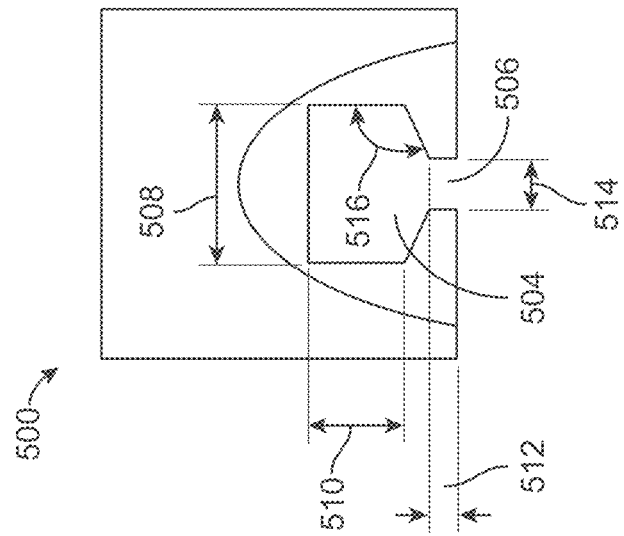
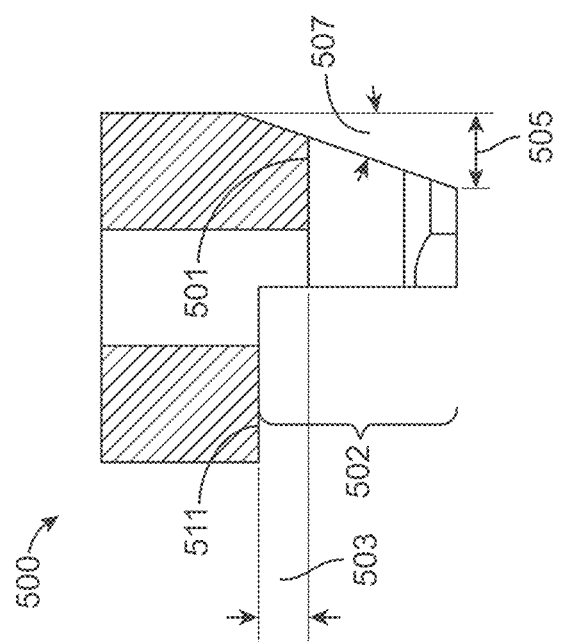
FIG. 5B
FIG. 5A

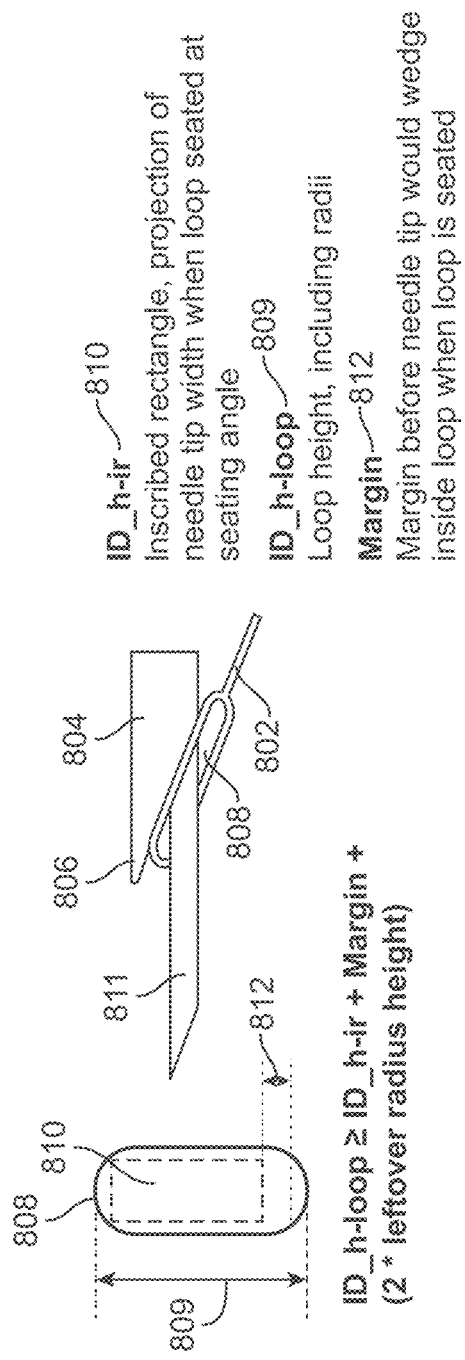
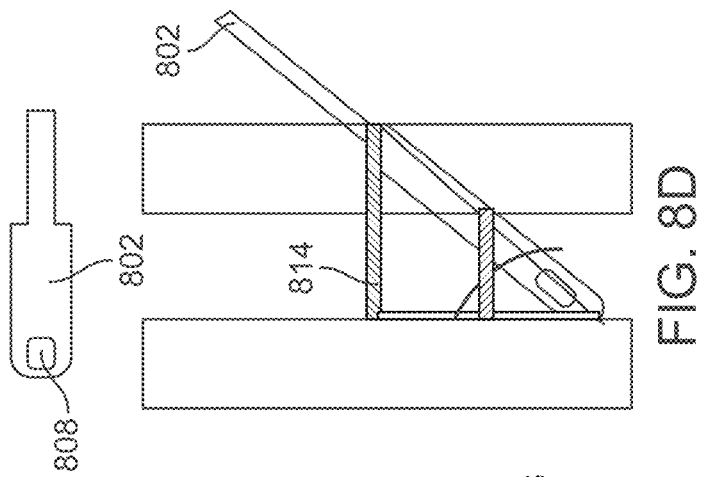
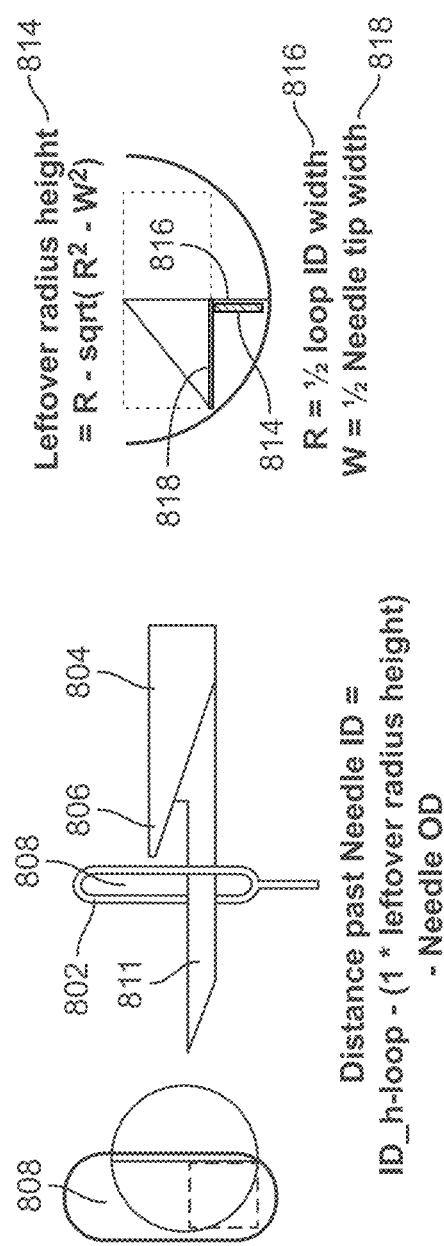

ID_h-ir — 810 Inscribed rectangle, projection of needle tip width when loop seated at seating angle ID_h-loop — 809 Loop height, including radii Margin — 812 Margin before needle tip would wedge inside loop when loop is seated

FIG. 8A $ID\_h\text{-}loop \geq ID\_h\text{-}ir + Margin + (2 * \text{leftover radius height})$

FIG. 8C

Leftover radius height — 814
$= R - \sqrt{R^2 - W^2}$
$R = \frac{1}{2}$ loop ID width — 816
$W = \frac{1}{2}$ Needle tip width — 818

FIG. 8B

Distance past Needle ID =
$ID\_h\text{-}loop - (1 * \text{leftover radius height}) - \text{Needle OD}$

FIG. 8D

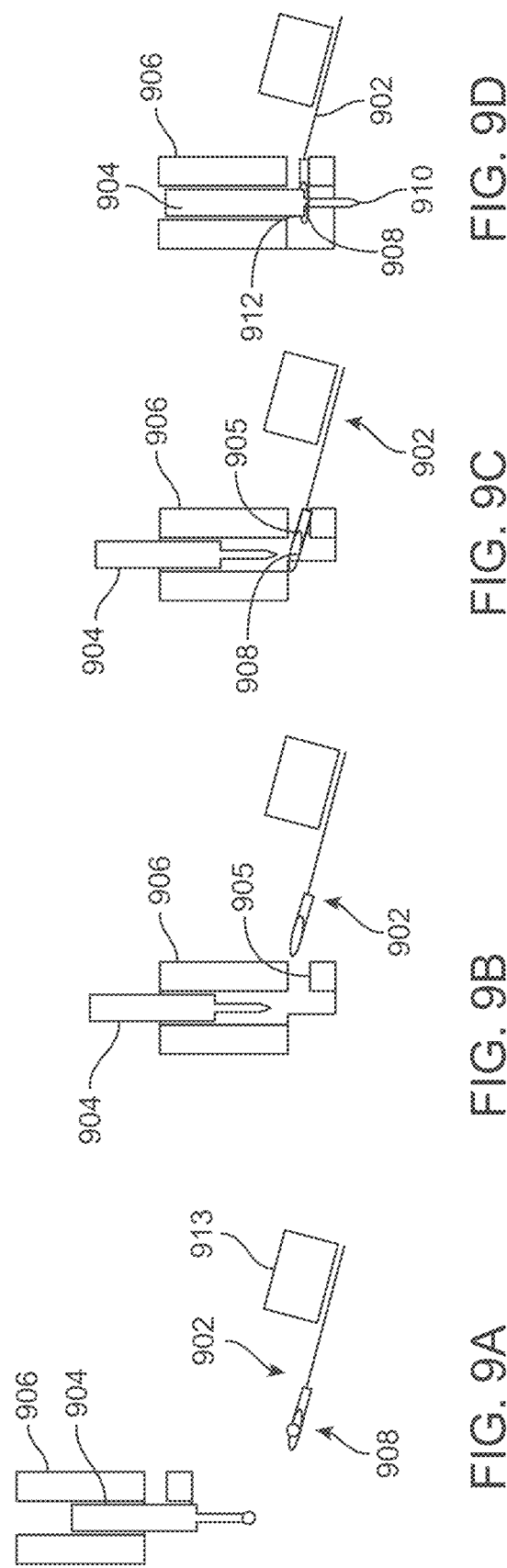

CANNULA FOR GRASPING AND SETTING LEAD WITH NEEDLE

CROSS-REFERENCES TO RELATED APPLICATIONS

Not applicable.

BACKGROUND

Brain-machine interfaces (BMIs) hold tremendous promise for the restoration of sensory and motor function and the treatment of neurological disorders. Most of these applications require fine scale communication—at the level of individual neurons—with large numbers of neurons across multiple brain areas. Advanced neural interfaces will require increasing the number of accessible neurons by many orders of magnitude over what is available by current methods. Thus, advanced neural interfaces require implantation of multiple el leads bearing electrodes in the brain in precise locations. Implanting these leads requires extreme precision on the micron or sub-micron scale. In order to achieve accurate implantation, each lead should be held firmly in place while guiding it to its destination. The equipment used to guide the leads into place should be cleanly detached from the needle after the lead is implanted, while maintaining a low profile in the sensitive implantation region.

BRIEF SUMMARY

In some embodiments, a system for implanting a device into biological tissue includes a biocompatible lead having an opening at one end surrounded by an expanded region; a needle having a ledge in a side of the needle; a cannula into which a portion of the needle is held and can extend or retract therein; and an exit gate protruding from an end of the cannula, the exit gate having an aperture on a side opposite the needle ledge and sized to accept the expanded region of the lead, the exit gate having a slot from the aperture to outside, wherein when the expanded region of the biocompatible lead is threaded through the exit gate aperture, the needle is configured to extend through the opening of the lead and catch the lead on the ledge, wherein the needle is further configured to extend past the exit gate of the cannula while pulling the lead through the slot and free of the aperture.

In some aspects, the system further includes a temporary attachment surface holding the lead from which the needle and exit gate can peel the lead. In some aspects, the biocompatible lead is a first lead, and the system further includes a plurality of leads including the first lead and a temporary attachment surface removably coupled to the plurality of leads, wherein the system is configured to implant each lead of the plurality of leads.

In some aspects, the cannula further comprises an indentation on a second side of the cannula. In some aspects, the expanded region of the lead is about 1.5 times to 5 times wider than a second region of the lead. In some aspects, the opening of the lead has a first height and the expanded region of the lead has a second height greater than the first height. In some aspects, the second height is about 3 times to 4 times the first height.

In some aspects, the system further includes a circuitry assembly disposed on a cranium and connected to a first end of the lead and an electrode for implantation in a brain of the cranium and connected to a second end of the lead. In some aspects, the circuitry assembly further includes an antenna configured to relay data.

In some aspects, the system further includes a robotic arm configured to position and implant the needle; a camera; and a microprocessor controller configured to control the robotic arm and the needle using the camera in order to engage the lead with the needle; pierce the biological tissue with the needle and the lead; and withdraw the needle while leaving the lead within the biological tissue.

In some embodiments, a method of implanting a device into biological tissue using a needle having a ledge in a side of the needle and a cannula having an exit gate protruding from an end of the cannula, the exit gate having an aperture on a side opposite the needle ledge and a slot from the aperture to outside, includes retracting the needle into the cannula; threading an expanded region of a biocompatible lead through the exit gate aperture, the expanded region surrounding an opening in the lead; threading the expanded region of a biocompatible lead through the exit gate aperture to position the opening of the lead beneath the needle; driving the needle through the opening of the lead and catching the lead on the ledge; pulling the expanded region of the lead from the exit gate aperture, through the slot, and free of the exit gate; piercing the biological tissue with the needle and the lead; disengaging the lead from the needle; and withdrawing the needle while leaving the lead within the biological tissue.

In some aspects, the method further includes peeling the lead from a temporary attachment surface through motion of the needle and the cannula. In some aspects, multiple leads are disposed on the temporary attachment surface; and the method further comprises peeling and implanting each of the multiple leads. In some aspects, a first end of the lead terminates in the opening; a second end of the lead terminates within a circuitry assembly; and the method further comprises disposing the circuitry assembly proximate to the biological tissue.

In some aspects, the circuitry assembly further comprises an antenna configured to relay data. In some aspects, the needle is driven through the opening by controlling a robotic arm based on position information gathered using a camera. In some aspects, the needle engages with the lead via motion of the needle according to a single degree of freedom. In some aspects, the expanded region of the lead is about 1.5 times to 5 times wider than a second region of the lead. In some aspects, the opening of the lead has a first height; and the expanded region of the lead has a second height about 3 times to 4 times the first height. In some aspects, the lead is left within the biological tissue at a depth of about one to about thirty millimeters.

BRIEF DESCRIPTION OF THE DRAWINGS

Illustrative aspects of the present disclosure are described in detail below with reference to the following drawing figures. It is intended that embodiments and figures disclosed herein are to be considered illustrative rather than restrictive.

FIG. TA illustrates view of a cannula, needle, and lead in a first configuration, according to an aspect of the present disclosure.

FIG. 3A illustrates another view of a cannula, needle, and lead, according to an aspect of the present disclosure.

FIG. 3B illustrates another view of a cannula, needle, and lead, according to an aspect of the present disclosure.

FIG. 3C illustrates a cross-sectional perspective view of a cannula, needle, and lead, according to an aspect of the present disclosure.

FIG. 5A illustrates a close-up side view of a cannula, according to an aspect of the present disclosure.

FIG. 5B illustrates a close-up front view of a cannula, according to an aspect of the present disclosure.

FIG. 8A illustrates a close-up view of a lead and needle, according to an aspect of the present disclosure.

FIG. 8B illustrates another close-up view of a lead and needle, according to an aspect of the present disclosure.

FIG. 8C illustrates example geometry of a lead and needle, according to an aspect of the present disclosure.

FIG. 8D illustrates another close-up view of a lead and needle, according to an aspect of the present disclosure.

FIG. 9A illustrates a needle, cannula, and lead before engagement, according to an aspect of the present disclosure.

FIG. 9B illustrates a needle, cannula, and lead moved toward a position for engagement, according to an aspect of the present disclosure.

FIG. 9C illustrates a needle and cannula and a lead moved to a position for engagement, according to an aspect of the present disclosure.

FIG. 9D illustrates a needle and cannula moved to engage with a lead, according to an aspect of the present disclosure.

DETAILED DESCRIPTION OF THE INVENTION

Figure 1A:
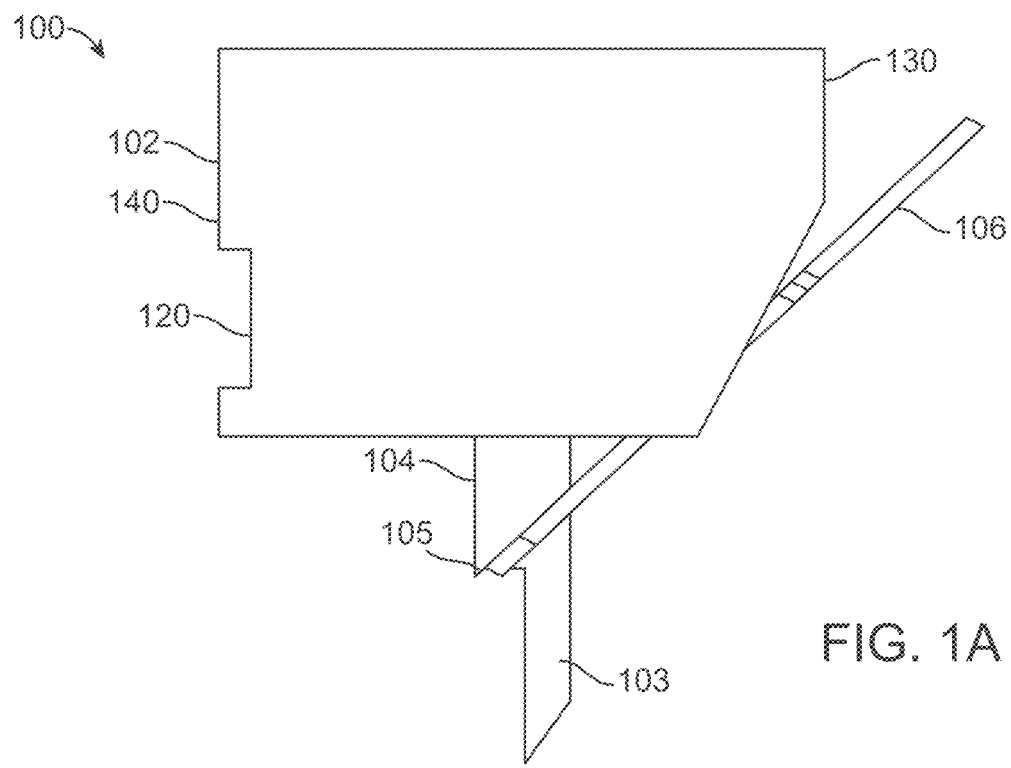
FIG. 1B illustrates another view of a cannula, needle, and lead in a first configuration, according to an aspect of the present disclosure.

The present disclosure relates to systems and methods for setting and implanting a lead. The lead can include electrodes that are configured to record and/or stimulate biological tissue. For example, each lead contains many wires, each containing an electrode. In some embodiments, biological tissue can include neurological tissue (also referred to as "brain tissue"). "Implanting a lead" may refer to implanting at least a portion of a lead into tissue. Alternatively, or additionally, implanting a lead may include disposing a portion of a lead on, or in proximity to, tissue.

Conventional approaches to implanting devices into neurological tissue suffer from several limitations. Conventional brain implants with electrodes tend to have a limited depth of penetration and limited targeting ability. In some prior systems, probe devices are fabricated in rigid two-dimensional (2D) arrays, which cannot be arranged with sufficient flexibility to, for example, be targeted to avoid blood vessels. The limited targeting ability also means that the electrodes as part of conventional structures or 2D arrays cannot be targeted or placed at dynamically selected or arbitrarily selected positions throughout the brain.

As noted above, implanting leads into brain for advanced BMIs requires extreme precision on the micron or sub-micron scale. In order to achieve accurate implantation, each lead should be held firmly in place while guiding it to its destination, and the equipment used to guide the lead into place should be cleanly detached from the needle. Some prior systems (e.g., as described in U.S. Patent Publication US-2020-0086111-A1, titled "Device Implantation Using A Cartridge," which is incorporated by reference) use a mechanism such as a pincer to hold the lead in place as it is positioned for implantation. While this serves very well to hold the lead in place and guide it to an accurate position, additional mechanical components create more room for mechanical failures and add complexity to the system. Additional mechanical components may require multiple degrees of freedom in the implantation process, which adds complexity of additional motors, controls, and routing. Moreover, using an additional component such as a pincer necessitates clearance to move the pincer around, which can cause entanglement with other leads. For example, a pincer can inadvertently catch and/or dislodge a previously implanted lead when multiple leads are being implanted.

Techniques described herein address these issues using a specialized cannula, lead, and needle configuration that can be used to hold the needle in place until implantation without additional components. Specialized systems can manipulate, aim, and implant these leads, as it would be difficult to impossible to implant such micron-scale leads manually. Using the geometry of the cannula, lead, and needle to hold the lead in place can reduce the number of degrees of freedom from three to one, simplifying the system and reducing room for failures. Accordingly, holding the lead in place using geometry of the components rather than an additional component helps remove failure modes and facilitates implantation of multiple leads in close proximity to one another.

In some embodiments, the needle can disengage with the lead once the lead is implanted, leaving only a flexible electrode array in contact with the biological tissue, thereby reducing the chronic micro-motion, scarring, and loss of recording/stimulating effects common to conventional approaches. Additionally, in some embodiments, the lead can be implanted using the needle and guidance from robotic surgery techniques.

Many of the details, dimensions, angles and other features shown in the Figures are merely illustrative of particular embodiments. Accordingly, other embodiments can include other details, dimensions, angles and features without departing from the spirit or scope of the present invention. Various embodiments of the present technology can also include structures other than those shown in the Figures and are expressly not limited to the structures shown in the Figures. Moreover, the various elements and features shown in the Figures may not be drawn to scale. In the Figures, identical reference numbers identify identical or at least generally similar elements.

As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as shown in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, terms such as "below" can encompass both an orientation of above and below, depending on the context of its use. The device may be otherwise oriented (rotated 90 degrees or at other orientations) and the spatially relative descriptors used herein are interpreted accordingly.

Although the terms "first", "second", etc. may be used herein to describe various elements, components, regions, layers and/or sections, it should be understood that they should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As used herein, the terms "and/or" and "at least one of" include any and all combinations of one or more of the associated listed items.

As used herein, the terms "approximately" and "about" are used to provide flexibility to a numerical range endpoint by providing that a given value may be within a functional range greater than or less than the given value. As used herein, unless otherwise specified, the given value modified by approximately or about is modified by ±10%.

Systems for Grasping and Setting a Needle with a Lead Using Cannula

Figure 1B:
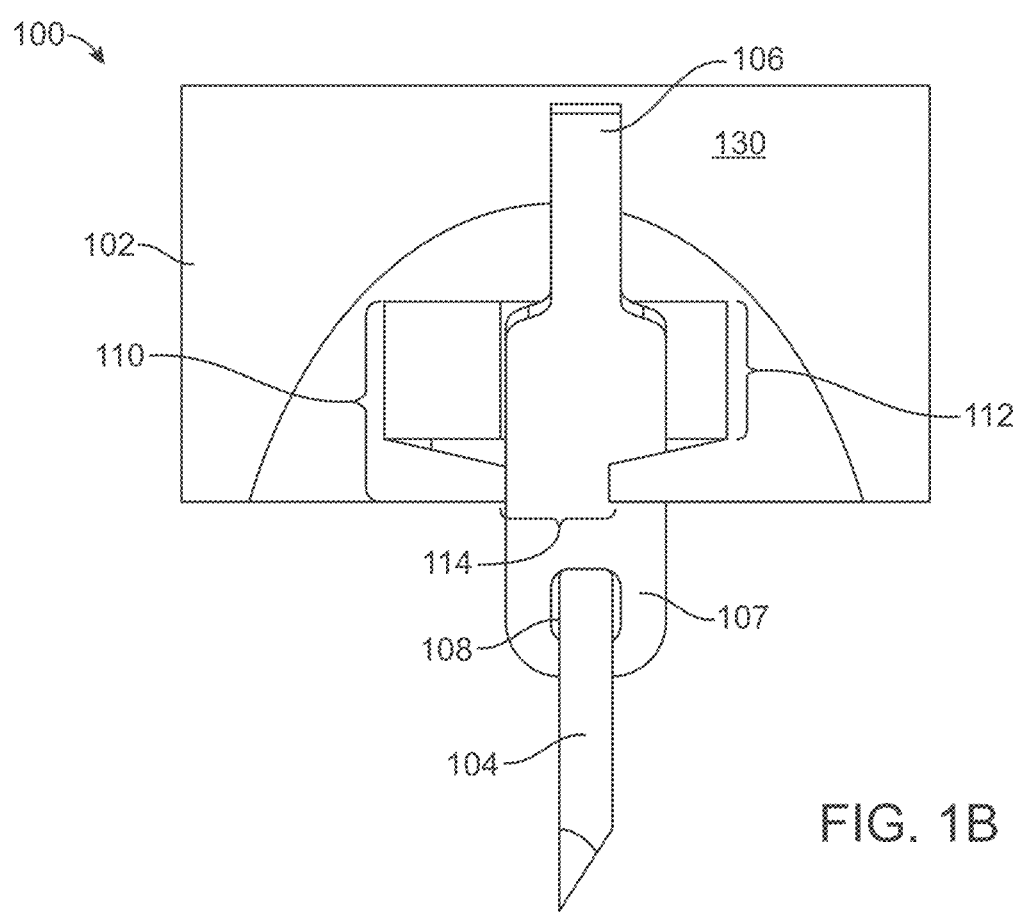

FIGS. 1A and 1B illustrate a system 100 for implanting a device into biological tissue, including a cannula 102, a needle 104, and a lead 106 in a first configuration, according to an aspect of the present disclosure. The cannula 102, needle 104, and lead 106 are shaped so that the lead 106 will be engaged and held in place by the cannula 102 and needle 104 until implantation, then disengaged.

Referring now to FIG. 1A, a side view of the system 100 is shown. The cannula 102 is configured to hold the needle 104. The cannula 102 may be a tube sized to fit the needle 104. For example, the cannula 102 can have a hollow region within which the needle 104 can be placed and move up and down (as shown in FIG. 3C). The needle 104 can extend or retract within the cannula 102. The cannula 102 includes an exit gate 110 in a first side 130 of the cannula opposite the ledge 105 of the needle 104. The cannula 102 further includes an indentation 120 on a second side 140 of the cannula opposite the exit gate 110.

The indentation 120 allows an opening 108 (shown in FIG. 1B) of the lead 106 to be centered under the needle 104 without risk of colliding into the back wall of the cannula 102. The indentation 120 may cover part of the back wall of the cannula 102, as shown in FIG. 1A. In alternative implementations, the indentation 120 is larger, effectively removing the back wall of the cannula 102 (see the indentation 402 of FIG. 4A). Other advantages of the indentation 120 include enabling better visibility of the process of threading the lead 106 through the needle 104, especially in debugging. The indentation 120 can also provide clearance to adjacent already-inserted leads.

Referring now to FIG. 1B, the exit gate 110 of the cannula 102 can be seen from a front view of the system 100. The exit gate 110, by way of specialized geometry, allows the needle 104 and lead 106 to exit the cannula 102 for implantation, and enables the lead 106 to be held in place when positioning the cannula 102, lead 106, and needle 104 for implantation. As shown in FIG. 1B, the exit gate 110 protrudes from the end of the cannula. The exit gate 110 includes an aperture 112 on one side of the cannula and a slot 114 from the aperture to outside. As shown in FIG. 1B, the aperture 112 can be an opening near an end of the cannula. The aperture 112 can connect to the slot 114 so that the aperture 112 and slot 114 lead out from the hollow region of the cannula 102.

The needle 104 includes a ledge 105 in a side of the needle. The ledge 105 is a notch configured to hold the lead in place when the needle 104 is threaded through the needle 104, resting on the ledge 105 and the exit gate 110 of the cannula 102. The ledge 105 may be milled. As shown in FIGS. 1A and 1B, the needle 104 can include a tip of a first width, a body of a second width, and the ledge 105 separating the two regions. Further details on examples of suitable needle 104 dimensions are described below with respect to FIG. 8.

The lead 106 may be a biocompatible lead. For example, the lead 106 is composed of biocompatible material such as polyimide or other polymeric material. In some implementations, the lead 106 is a thin piece of polymer including one or more biocompatible thin film materials. The lead 106 may include conductive material to transmit information. For example, the lead 106 may include a gold thin film trace. In some embodiments, the gold thin film trace is encased in polyimide substrate. For example, a thin film layer of polyimide is deposited, then a gold thin film layer is deposited, then another thin film layer of polyimide is deposited, such that the gold thin film layer is sandwiched between the polyimide layers. In some embodiments, the lead 106 may include up to three layers of insulation and two layers of conductor.

The lead 106 may include may wires, each embedded with one or more extremely small and fine electrodes. Electrodes are small pieces of electrically conductive materials. For example, each lead contains 16 wires, one for each of the 16 electrodes it contains. The electrodes may be configured for recording and/or stimulation of biological tissue (e.g., stimulating neurons in the brain and recording neural spikes from the brain). Alternatively, or additionally, the lead 106 may be dispersed with other conduits for conducting information, such as a wave guide or microfluidic channel. In some embodiments, the electrodes (or other conduits) are spaced by approximately 50 µm, 75 µm, and/or between 25-100 µm. The lead 106 may include approximately 32 electrodes 407 and/or between 1-100 electrodes or 25-75 electrodes. The electrodes may be configured to be inserted into biological tissue (e.g., biocompatible and/or sized to be inserted into biological tissue).

As shown in FIG. 1B, the lead 106 has an opening 108 at one end surrounded by an expanded region 107. The opening 108 is sized to fit the needle 104. The expanded region 107 is sized and shaped so that the lead can be held in place via the exit gate 110 of the cannula 102. Further details on examples of suitable lead 106 dimensions are described below with respect to FIG. 6. As shown in FIG. 1B, when fixed in place by the needle ledge 105 and exit gate 110, the lead may be seated in place at a particular seating angle with respect to the needle 104.

The aperture 112 of the cannula 102 may be on a side opposite the needle ledge 105 and sized to accept the expanded region of the lead 106. As shown in FIG. 1A and FIG. 1B, the lead 106, needle 104, and cannula 102 are positioned so that the lead 106 catches on the ledge 105 of the needle 104 and the exit gate 110 of the cannula 102. This can be a first configuration where the needle 104 and the lead 106 are held in place via the respective geometry and position of the lead 106, needle 104, and cannula 102. In the configuration shown in FIGS. 1A and 1B, when the expanded region 107 of the lead 106 is threaded through the exit gate aperture 112, the needle 104 is configured to extend through the opening 108 of the lead 106 and catch the lead 106 on the ledge 105. In some implementations, the needle 104 and the cannula 102 are provided as a cannula and needle assembly, which can be a single consumable device.

Figure 2A:
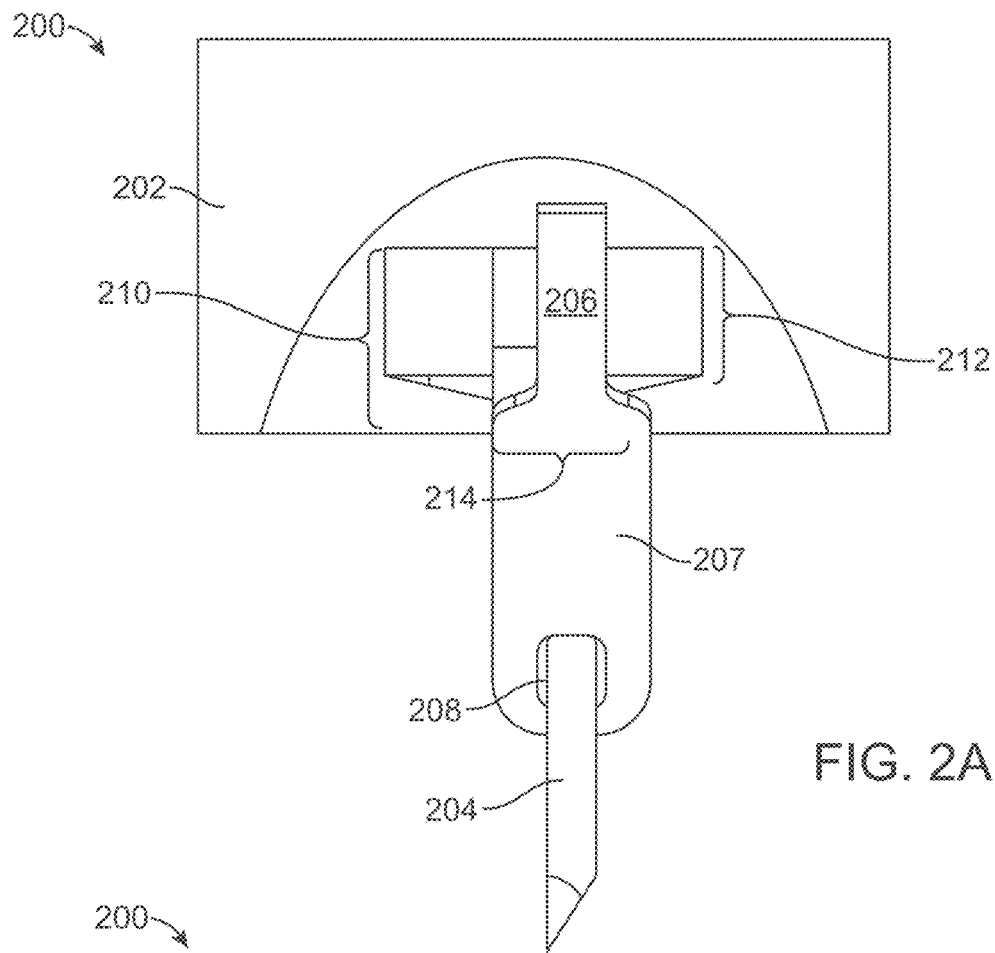
FIG. 2A illustrates a view of a cannula, needle, and lead in a second configuration, according to an aspect of the present disclosure.
Figure 2B:
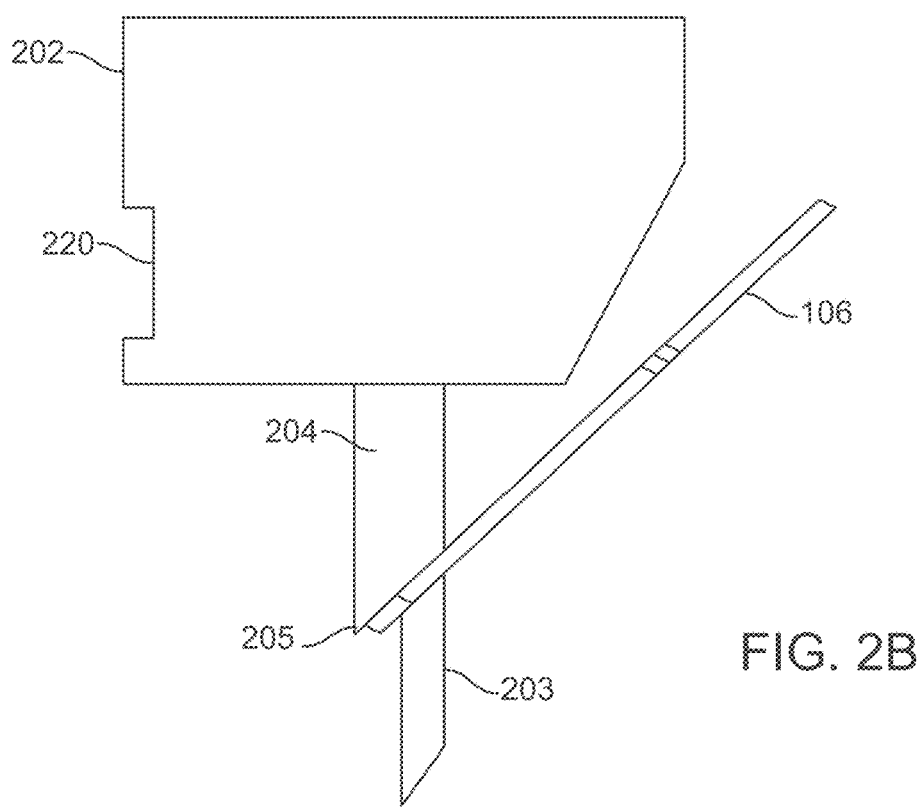
FIG. 2B illustrates another view of a cannula, needle, and lead in a second configuration, according to an aspect of the present disclosure.

FIGS. 2A and 2B illustrate a cannula 202, needle 204, and lead 206 in a second configuration, according to an aspect of the present disclosure. In the configuration illustrated in FIGS. 2A and 2B, the needle 204, coupled to the lead 206, is positioned lower with respect to the cannula 202. In this position, the lead 106 is no longer held in place by the cannula 202. This position can be used to release the lead 206, e.g., for implantation. In this configuration, the needle 204 extends past the exit gate of the cannula 202 while pulling the lead 206 through the slot and free of the aperture.

FIGS. 3A, 3B, and 3C illustrate additional images depicting a cannula and needle assembly 300 including a cannula 302 and needle 304, according to an aspect of the present disclosure. FIG. 3A shows a side view of the cannula 302 and the needle 304. The needle 304 is extended down through the bottom of the cannula 302. The needle 304 includes a ledge 305. A scale 306 of 100 micrometers (µm) is shown for reference. The needle 304 is extended 150 µm out of the cannula 302 in this example. This is one example of a suitable scale, and other scales may be implemented.

FIG. 3B shows a front view of the cannula 302 and needle 304. The needle 304 is extended down through the bottom of the cannula 302. An exit gate 308 in the cannula is configured such that a lead (not shown in FIG. 3B) can extend through the exit gate 308 and be held in place via the geometry of the exit gate 308, lead, and needle 304.

FIG. 3C shows a cross-sectional perspective view of the cannula 302 and needle 304. In FIG. 3C, the needle 304 is retracted within the cannula 302. The needle 304 is visible inside the cannula 302 in this cross-sectional view. The cannula is shaped so that the needle 304 can move up and down in the cannula 302. For example, as shown in FIG. 3C, the cannula 302 is cylindrical in shape with a cylindrical cavity 310 sized to fit the needle 304.

Figure 4A:
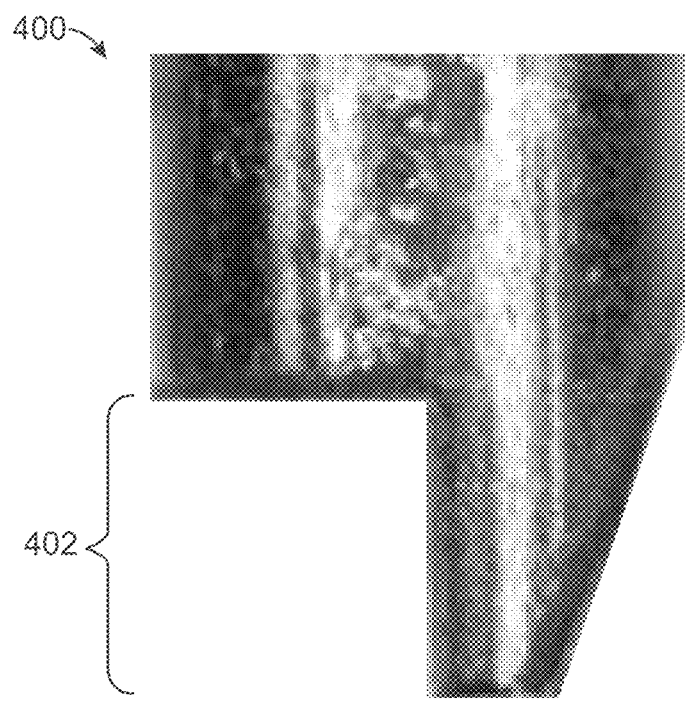
FIG. 4A is a photograph of a cannula depicting a side view, according to an aspect of the present disclosure.
Figure 4B:
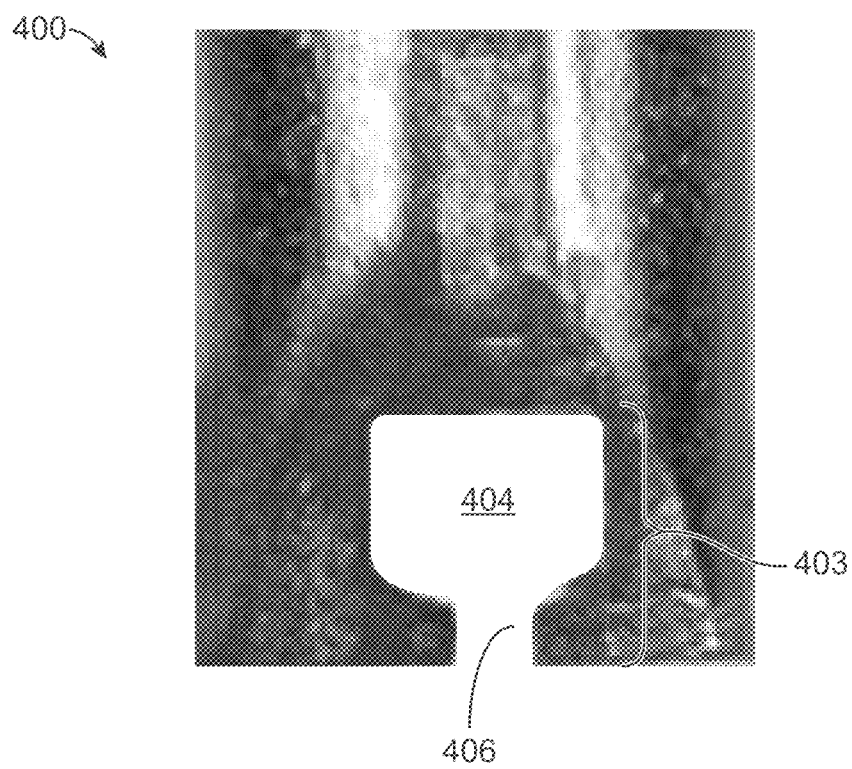
FIG. 4B is a photograph of a cannula depicting a front view, according to an aspect of the present disclosure.

FIGS. 4A and 4B are photographs of a cannula 400, according to an aspect of the present disclosure. FIG. 4A depicts a side view of a cannula 400. The cannula 400 includes an indentation 402 in one side of the cannula 400. As described above with respect to FIG. 1A, when threading a lead, the indentation 402 allows the opening of the lead to be centered under the needle 104 without risk of colliding into the back wall of the cannula, as well as enabling better visibility of the process of threading the lead 106 through the needle 104, and providing clearance to adjacent already-inserted leads.

FIG. 4B depicts a front view of the cannula 400. In the front view, an exit gate 403 including an aperture 404 and a slot 406 from the aperture 404 to outside of the cannula 400 can be seen. The cannula may be milled to include the aperture 404 and slot 406.

FIGS. 5A and 5B illustrate close-up views of a cannula 500, according to an aspect of the present disclosure. FIG. 5A depicts a side view of the cannula 500. The cannula 500 includes an indentation 502 for providing clearance during the implantation process. The indentation 502 may be a blasted cut in the cannula 500. FIG. 5B depicts a front view of the cannula 500, showing an aperture 504 in the cannula 500 and a slot 506 from the aperture 504 to outside of the cannula 500.

In some implementations, the indentation 502 is higher than the aperture 504. As shown in FIG. 5A, the spacing 503 from the top 501 of the aperture 504 to the top 511 of the indentation 502 can be less than 0.1 µm, e.g., approximately 0.030 µm. The indentation 502 is higher than the aperture 504 to mitigate risk of the expanded region of the lead (e.g., as shown in FIGS. 1A and 1B) from clipping on the rear wall of the cannula 500. The indentation 502 also can facilitate cleaning and improve visibility (e.g., using cameras as depicted in FIGS. 12A-13B). In some implementations, the aperture 504 is inclined at an angle of about 10 degrees to about 30 degrees, e.g., approximately 20 degrees. As shown in FIGS. 1B and 2B, this angle is suitable to hold the lead in place when the needle is retracted in the cannula 500 and release the lead when the needle is lowered out of the cannula 500. This may correspond to a distance 505 of about 0.33 µm, depending on the scale of the cannula 500.

Referring now to FIG. 5B, some additional example relative scales are shown. It should be understood that the size of the cannula may be scaled up or down, so long as the ratios remain in the specified range, while providing the lead-fixing abilities described herein. As shown in FIG. 5B, for example, a suitable aperture width 508 of the aperture 504 may be less than 0.1 µm, e.g., approximately 0.069 µm. A suitable aperture height 510 can be approximately ⅔ the aperture width 508, e.g., approximately 0.04 µm. The slot height 512 of the slot 506 can be approximately ¼ the aperture height, e.g., approximately 0.011 µm. The slot width 514 of the slot 506 can be approximately twice the slot height 512, e.g., approximately 0.022 µm. The aperture 504 can further include inclined angles at the bottom of the aperture 504 in order to hold the lead and needle in place.

For example, as illustrated in FIG. 5B, a suitable angle of inclination is about 115 degrees from the aperture bottom to the aperture wall.

Figure 6:
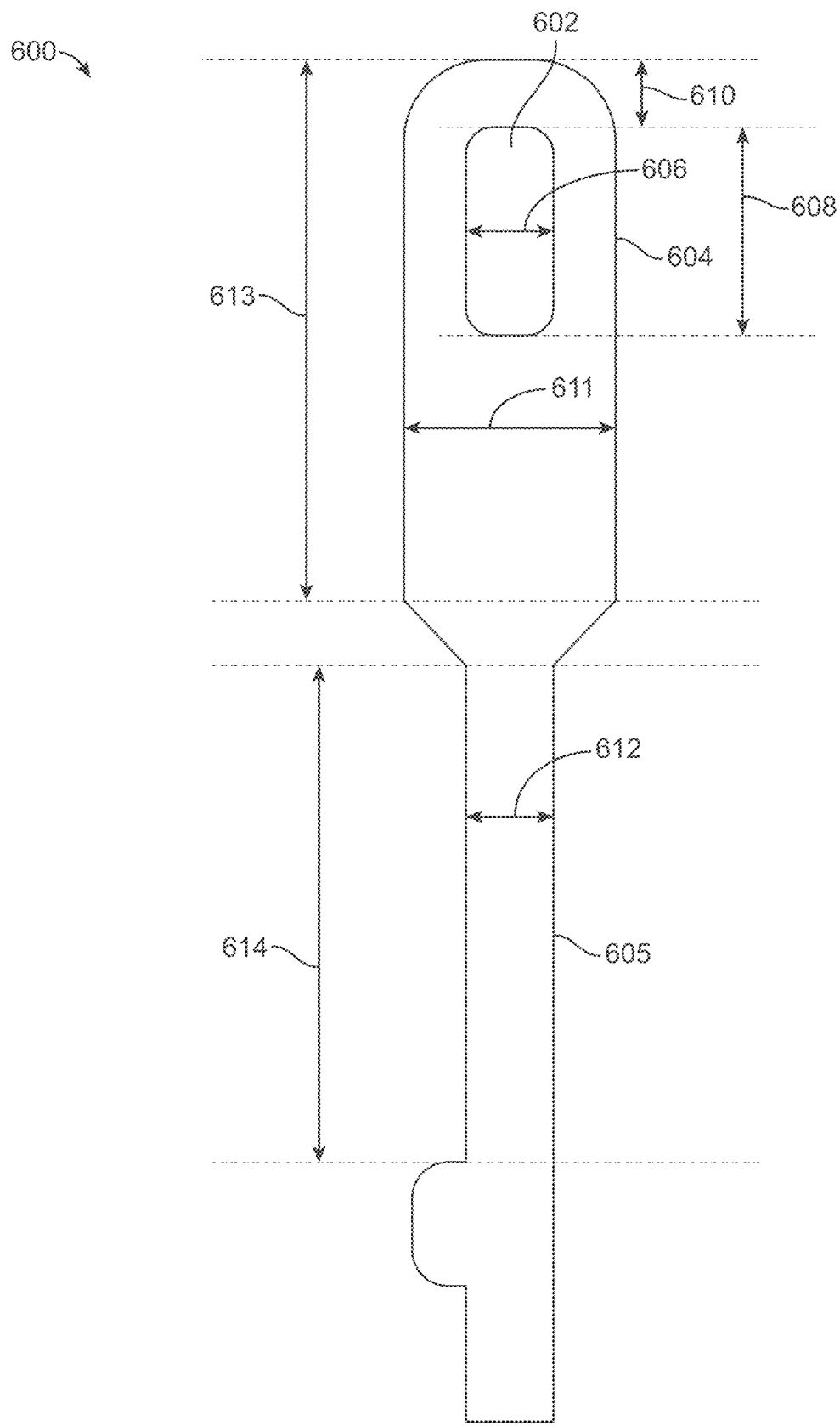
FIG. 6 illustrates a lead with an expanded region, according to an aspect of the present disclosure.

FIG. 6 illustrates a lead 600 with an expanded region 604, according to an aspect of the present disclosure. As described above, the expanded region 604 is a portion of the lead 600 that has an increased thickness in a region of the lead 600 near an opening 602 in the lead 600. The lead 600 also includes a second region 605 with a different thickness than the expanded region 604.

Figure 7:
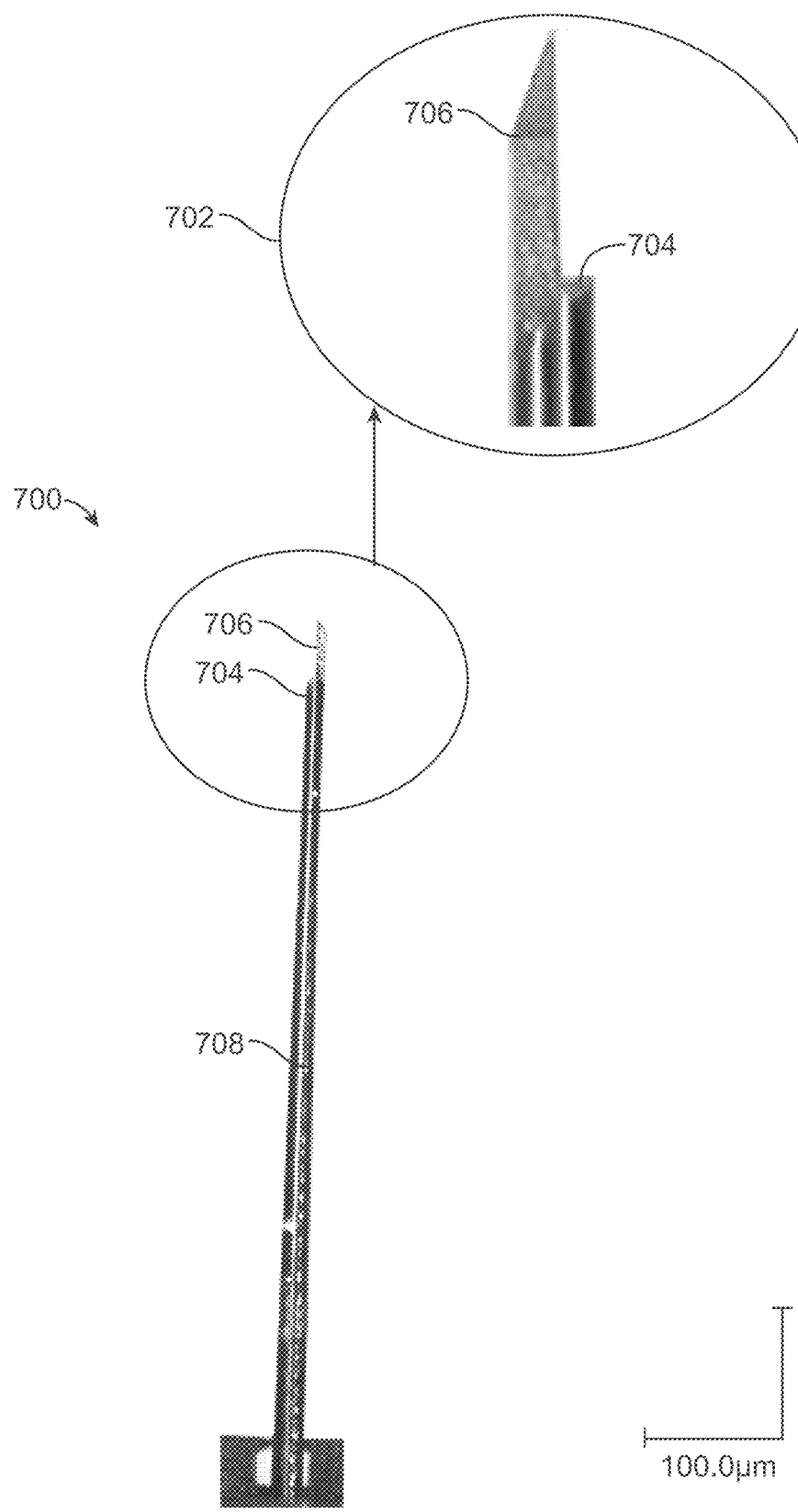
FIG. 7 illustrates a needle with a ledge, according to an aspect of the present disclosure.

FIG. 6 shows example dimensions for the lead 600. These dimensions have been found to successfully hold the lead 600 in place when the needle is partially extended out of the cannula, and release the lead 600 when the needle is retracted after implantation. In the example depicted in FIG. 6, an example lead 600 geometry is shown. This scale lead 600 is appropriate for use with a needle of between about 10 to 30 µm in width, for example, 24 µm in width, where the width refers to the thicker part of the needle (e.g., the second portion 708 as shown in FIG. 7). If the needle is scaled up or down, the benefits described herein can be provided by scaling the lead geometry up or down accordingly.

In this example, the opening 602 has an opening width 606 of about 14 µm (i.e., between about 10 µm and 20 µm). The opening 602 has an opening height 608 (e.g., a first height) of about 40 µm (i.e., between about 30 µm and 50 am). This particular opening height 608 ratio has been found to minimize the risk of the opening 602 slipping while supporting a relatively aggressive seating angle (e.g., of about 65-35 degrees). The opening 602 should be sized so that the thinner part of the needle fits through the opening 602 and the ledge of the needle rests on the expanded region 604 of the lead 600. For example, an opening width 606 of about ½ to ⅔ the size of the needle width is suitable. An opening height 608 of about 1.5 to 2 times the size of the needle width is suitable. The distance 610 from the opening 602 to the end of the lead 600 proximate to the opening 602 is about 9 µm (e.g., about ⅓ the size of the needle width).

In the example shown in FIG. 6, the expanded region 604 of the lead 600 has a width 611 of about 32 µm (i.e., between about 25 µm and 40 µm) and an expanded region height 613 (e.g., a second height) of about 133 µm (i.e., between about 100 µm and 150 µm). The second height of the expanded region 613 is greater than the first height of the opening 608. An expanded region width 611 of about 1.1 to 1.5 times the size of the needle width is suitable. In particular, a suitable value for the expanded region width 611 is equal to twice the distance 610 plus the opening width 606. An expanded region height 613 of about 5 to 6 times the needle width is suitable. In some implementations, the height of the expanded region 613 is about 3 times to four times the height of the opening 608, and the width of the expanded region 611 is about 1.5 times to 5 times the width of the second region 612 (e.g., two times to three times the width of the second region 612, 1.5 times to 3 times the width of the second region 612, or 4 times to 5 times the width of the second region 612). This expanded region height 613 or ratio has been found to prevent premature exit of the cannula when the lead is seated.

In this example, the lead width 612 of the portion of the lead 600 shown in FIG. 6 is about 14 µm (e.g., in a range of about 10 µm to 20 µm), for a needle width of about 24 µm. The lead height 624 of the portion of the lead 600 shown in FIG. 6 can represent a length of lead that extends upwards for engagement with the needle. In some implementations, this height 624 is at least 150 µm so that the loop is visible for engagement with the needle (e.g., using computer vision techniques, as described in U.S. Patent Publication US-2020-0085508-A1, titled "Computer Vision Techniques," which is incorporated by reference herein).

FIG. 7 illustrates a needle 700 with a ledge 704, according to an aspect of the present disclosure. The needle 700 includes a first portion 706 having a first width shorter than a second width of a second portion 708. Between the first portion 706 and the second portion 708 is the ledge 704. As described above, the ledge 704 is configured to catch the lead. 100 µm is shown in the corner for scale.

FIGS. 8A, 8B, and 8C, and 8D illustrate close-up views showing a lead 802 and needle 804, according to an aspect of the present disclosure. FIGS. 8A-8D also show appropriate dimensions and geometries for the lead opening, according to some embodiments.

In FIG. 8A, the lead 802 is resting on the ledge 806 of the needle 804, which can help to hold the lead in place as described herein. When resting on the ledge 806, the opening 808 of the lead 802 is seated at a seating angle with respect to the needle 804. FIG. 8B shows the lead 802 moved to a position towards the tip 811 of the needle 804 (e.g., before catching on the ledge 806 or after removal from the ledge 806). At this position, the lead 802 is not necessarily held at the seating angle. For example, as shown in FIG. 8B, the lead 802 and is substantially perpendicular to the needle 804.

In FIGS. 8A-8D, the profile of the opening 808 of the lead 802 is shown. As illustrated in FIG. 8C, the opening 808 has a height ID_h-loop 809. ID_h-ir 810 is an inscribed rectangular projection of the tip 811 of the needle 804 width when the opening 808 of the lead 802 is seated on the ledge 806 of the needle 804 at the seating angle. ID_h-loop 809 is the height of the opening 808, including radii R (e.g., R=½ ID_h-loop). Margin 812 is a margin before the needle 804 tip 811 would wedge inside the opening 808 when seated. Based on these values, a leftover radius height 814 can be computed as $$R - \sqrt{(R^2 - W^2)}$$

where R=½ ID_h-loop and W=½ needle tip 811 width. FIG. 8D shows the leftover radius height 814 with respect to the lead 802 at the seating angle.

Engagement and Implantation Techniques

FIGS. 9A-9D illustrate engagement of a needle 904 with a lead 902, according to some embodiments. FIG. 9A illustrates a needle 904, cannula 906, and lead 902 before engagement, according to an aspect of the present disclosure. The lead 902 includes an opening 908 for engagement with the needle 904. The lead is further attached to a temporary attachment surface 913. The temporary attachment surface 913 may hold one or more leads removably in place for engagement with the needle 904. The temporary attachment surface 913 may, for example, be made of silicon, as further described below with respect to FIG. 10. The cannula 906 holds and moves the needle 904.

FIG. 9B illustrates the needle 904, cannula 906, and lead 902 lead moved toward a position for engagement, according to an aspect of the present disclosure. The needle 904 is retracted in the cannula 906. The lead 902 is moved towards an exit gate aperture 905 of the cannula 906.

FIG. 9C illustrates the needle 904, cannula 906, and lead 902 moved to a position for engagement, according to an aspect of the present disclosure. The lead 902 is inserted into the cannula 906 through the exit gate aperture 905. The opening 908 of the lead 902 is positioned below the needle 904.

FIG. 9D illustrates a needle 904 and cannula 906 moved to engage with a lead 902, according to an aspect of the present disclosure. The needle 904 is lowered so that the tip 910 of the needle 904 extends out of the cannula 906 and through the opening 908 of the lead 902. The lead 902 may rest on a ledge 912 of the needle 904.

Figure 10:
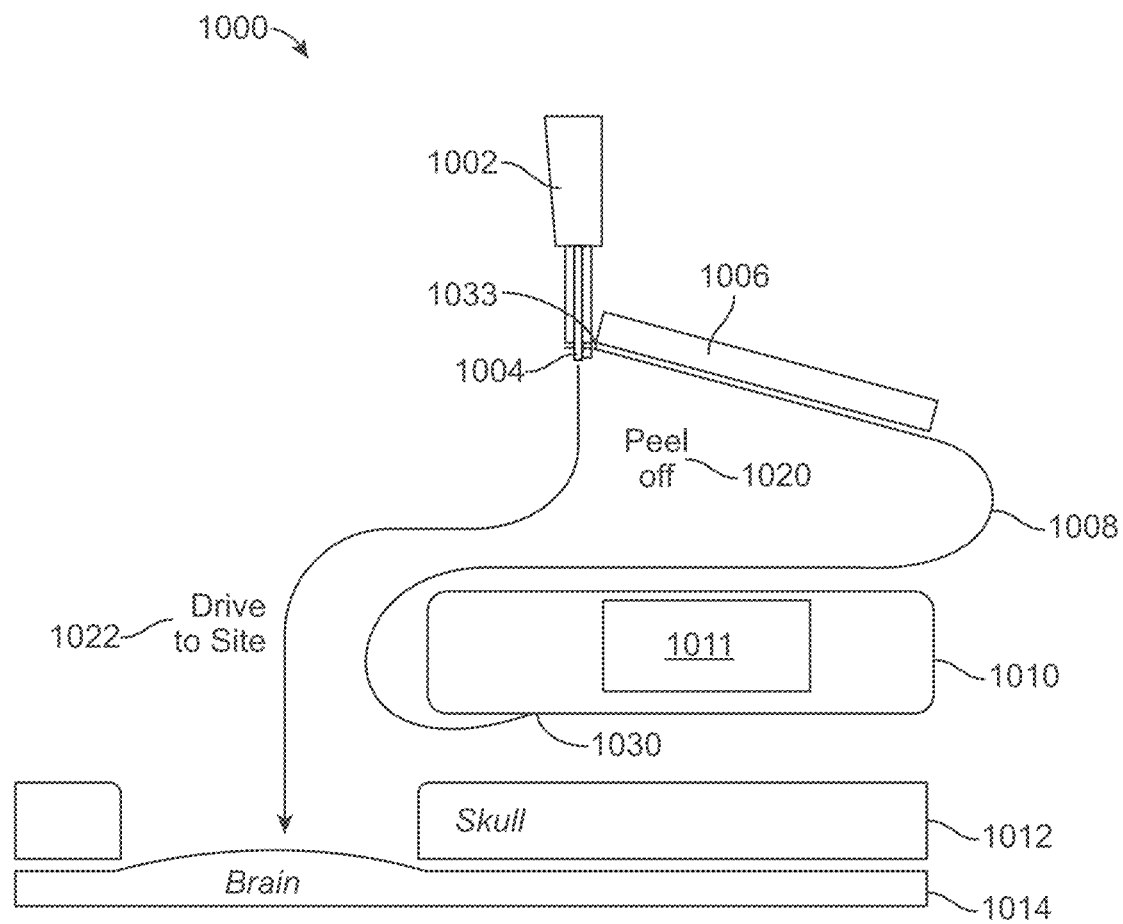
FIG. 10 illustrates implantation of a lead engaged with a needle and cannula, according to an aspect of the present disclosure.

FIG. 10 illustrates a schematic overview 1000 illustrating implantation of a lead 1008 engaged with a needle 1004 and cannula 1002, according to an aspect of the present disclosure. The lead 1008 is attached to a temporary attachment surface 1006. The temporary attachment surface 1006 may, for example, be a flexible backing composed of silicon or parylene. The temporary attachment surface 1006 holds one or more leads 1008 in place to be engaged with by the needle 1004. As described above, the needle 1004 can extend out of the cannula 1002 to catch the lead 1008. As the needle 1004 and cannula 1002 move together, the needle 1004 and cannula 1002 peel the lead 1008 off of the temporary attachment surface 1006 at operation 1020.

In some implementations, as depicted in FIG. 10, a circuitry assembly 1010 is attached to one end of the lead 1008. The circuitry assembly 1010 may include a storage package structure holding circuitry, which can have variable shapes and sizes, and can be configured to remain in vivo within a subject along with the circuitry assembly 1010 and lead(s) 1008 following implantation. The circuitry assembly 1010 can further include an antenna 1011 or other communications relay to transmit and receive data to and from the circuitry assembly 1010. The antenna 1011 can be configured to transmit on radio frequencies, Wi-Fi frequencies, or the like, in order to relay data, electricity (e.g. for charging the probe device), or other signals. Additionally, the circuitry assembly 1010 can include specially configured, application-specific integrated circuits such as those described in U.S. Patent Publication US-2019-0286592-A1, entitled "Network-On-Chip for Neurological Data", which is incorporated by reference.

In some implementations, an array of leads 1008 are connected to the circuitry assembly 1010. Within the circuitry assembly 1010, the leads 1008 may be connected as part of an overall probe device, where the electrodes are connected to each other and connected to the circuitry assembly 1010 with similarly small and fine filament-like connections. In some such aspects, the leads 1008 include electrodes extending out as terminal points arranged and configured to send and receive signals. In some aspects, the circuitry assembly 1010 with such a plurality of terminal electrodes covering the brain can be understood as akin to a multiplexer, having multiple inputs and directing signal individually or in aggregate through an output signal. The circuitry assembly 1010 can also be configured to deliver signals through the plurality of electrodes, effectively operating in the opposite direction of current or data.

The circuitry assembly 1010 may be disposed on a cranium 1012 (i.e., on a skull). A small opening is disposed in the cranium 1012. The lead 1008 is implanted in a brain 1014 of the cranium 1012 via the opening. The cannula 1002 and needle 1004 can move together to drive the lead 1008 to an implantation site in the brain 1014 at operation 1022. As described above, when the needle 1004 and cannula 1002 are pulled up away from the implantation site, the lead 1008 is disengaged from the needle 1004. The shape of the needle, cannula and lead can make the disengagement process simply occur as the needle 1004 and cannula 1002 are moved away from the implantation site. A first end of the lead 1030 is disposed in the circuitry assembly 1010, which is left near the implantation site (e.g., on or near the cranium 1012). A second end of the lead 1033 is left implanted in the brain 1014.

Figure 11:
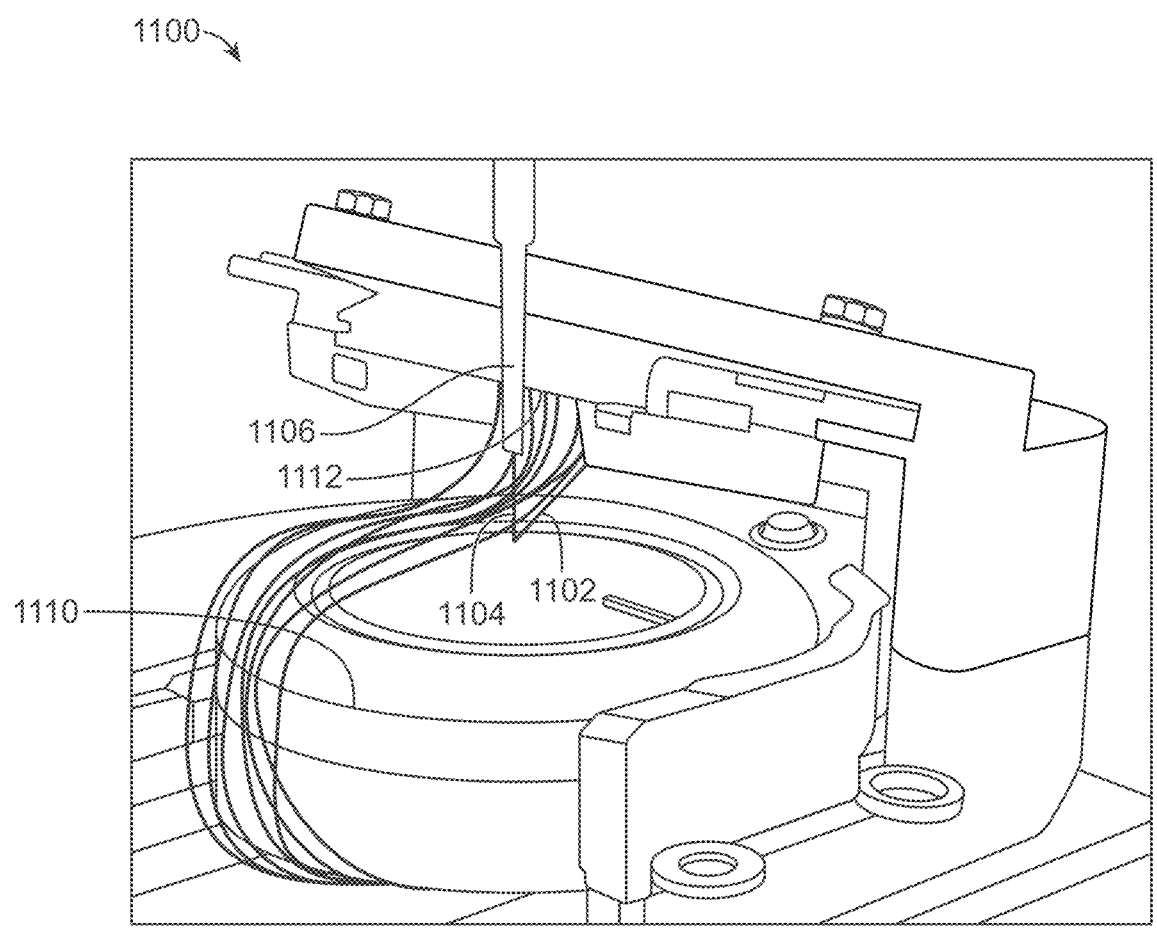
FIG. 11 illustrates multiple leads disposed for implantation, according to aspects of the present disclosure.

FIG. 11 is an example photograph 1100 illustrating multiple leads 1102 disposed for implantation by a needle 1004 according to aspects of the present disclosure. As shown and described above with respect to FIG. 10, the leads 1102 can initially be disposed on a temporary attachment surface 1112, and be peeled off using the needle 1104 and a cartridge 1106. Multiple leads 1102, one of which is being manipulated with the needle 1104 and cartridge 1106, are shown in FIG. 11. The multiple leads 1102 extend from a circuitry assembly 1110 at one end and the temporary attachment surface 1112 at another end.

Figure 12A:
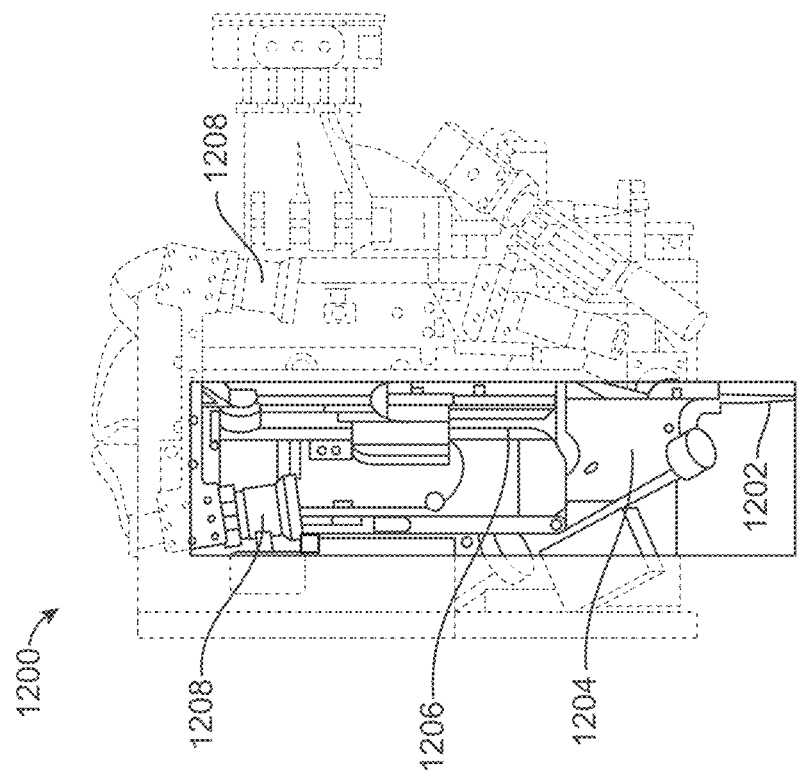
FIG. 12A illustrates a first view of an apparatus for implantation and engagement of a lead, according to an aspect of the present disclosure.

FIG. 12A illustrates an exploded cross-sectional exploded view of an apparatus 1200 for implantation and engagement of a lead, according to an aspect of the present disclosure. The apparatus 1200 can include a needle 1202, a cartridge 1204, and a robotic arm 1206 for actuating the needle 1202 and cartridge 1204. The robotic arm 1206 can include or be communicatively coupled to a motor (e.g., a linear motor) for moving the needle 1202 and cartridge 1204. In some aspects, the robotic arm 1206 is communicatively coupled to a microprocessor controller 1210 configured for managing motion of the robotic arm 1206, needle 1202, and cartridge 1204. In some aspects, the robotic arm 1206 moves the needle 1202 and cartridge 1204 based on a single degree of freedom (e.g., up and down), which reduces room for error and part failure. The apparatus 1200 may further include cameras 1208 for guiding implantation and lead engagement. The cameras 1208 can be used to guide a lead to a target region for implantation, as well as to guide the lead and the needle together to engage the lead. Techniques for automatic guiding of the needle and lead are described in "Computer Vision Techniques," supra.

Figure 12B:
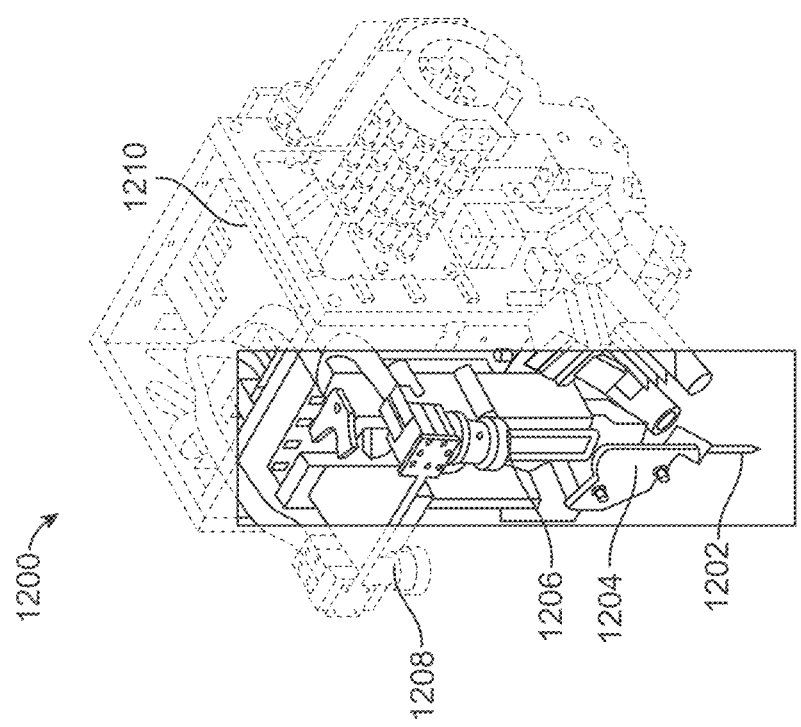
FIG. 12B illustrates a second view of an apparatus for implantation and engagement of a lead, according to an aspect of the present disclosure.

FIG. 12B illustrates a second view of the apparatus 1200 depicted in FIG. 12A according to an aspect of the present disclosure. The apparatus 1200, including needle 1202, cartridge 1204, robotic arm 1206, and camera 1208, are depicted in a side view.

Figure 13B:
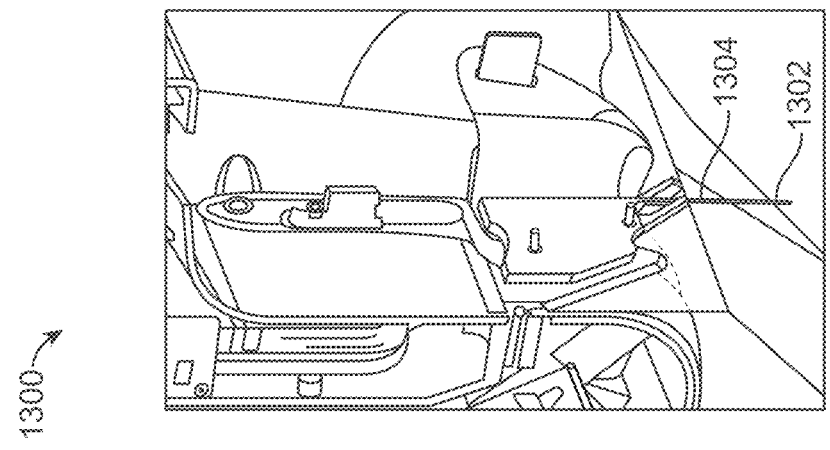
FIG. 13B illustrates a second close-up view of an apparatus for implantation and engagement of a lead, according to an aspect of the present disclosure.
Figure 13A:
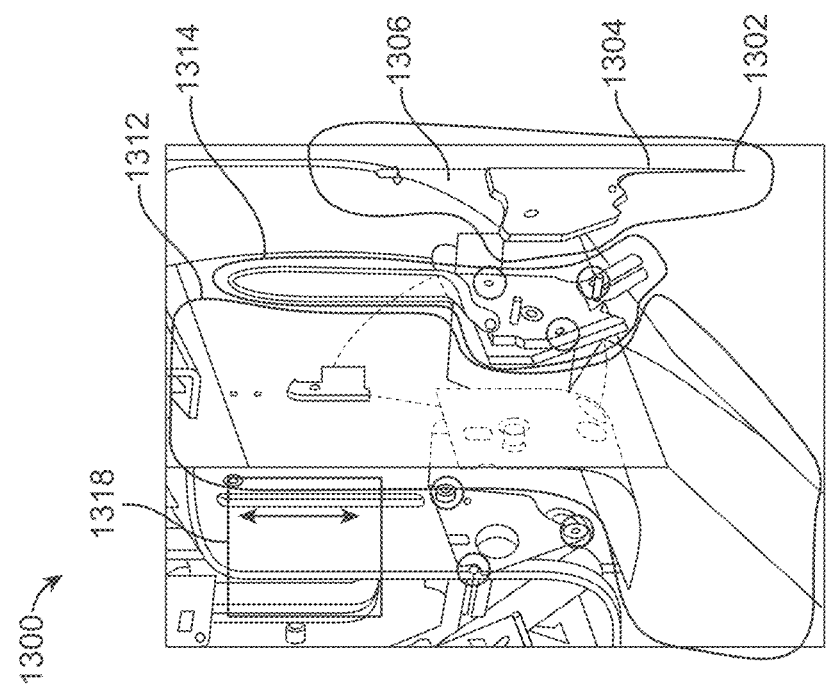
FIG. 13A illustrates a first close-up view of an apparatus for implantation and engagement of a lead, according to an aspect of the present disclosure.

FIG. 13A illustrates a first close-up view of an apparatus 1300 (e.g., the apparatus 1200 depicted in FIGS. 12A and 12B) for implantation and engagement of a lead, according to an aspect of the present disclosure. The apparatus 1300 includes a needle 1302, cartridge 1304, and robotic arm 1306, as described above with respect to FIG. 12A. Also shown in FIG. 13A are a drape 1312 and kinematic coupler 1314. The drape 1312 is a sterile drape. In some aspects, the drape 1312 is replaceable. The kinematic coupler 1314 redirects the imaging path from the cameras (e.g., cameras 1208 as shown in FIGS. 12A and 12B), as well as serving as a sterile mounting for the needle 1302 and cartridge 1304.

In some implementations, the robotic arm 1306 moves the needle 1302 along a single axis, while spanning a sterile field established by the drape 1312 and kinematic coupler 1314. The needle 1302 and cartridge 1304 mount on the robotic arm 1306, which may be driven by a motor 1318. In this position, the apparatus 1300 is capable of grasping and engaging the lead with the needle 1302, as well as inserting the needle 1302 and lead into biological tissue when positioned properly. The apparatus 1300 may move as a whole to position the needle 1302 and cartridge 1304 for implantation.

FIG. 13B illustrates a second close-up view of the apparatus 1300 according to an aspect of the present disclosure.

The apparatus 1300, including the needle 1302 and cartridge 1304, are depicted in a collapsed close-up cross-sectional side view.

Figure 14:
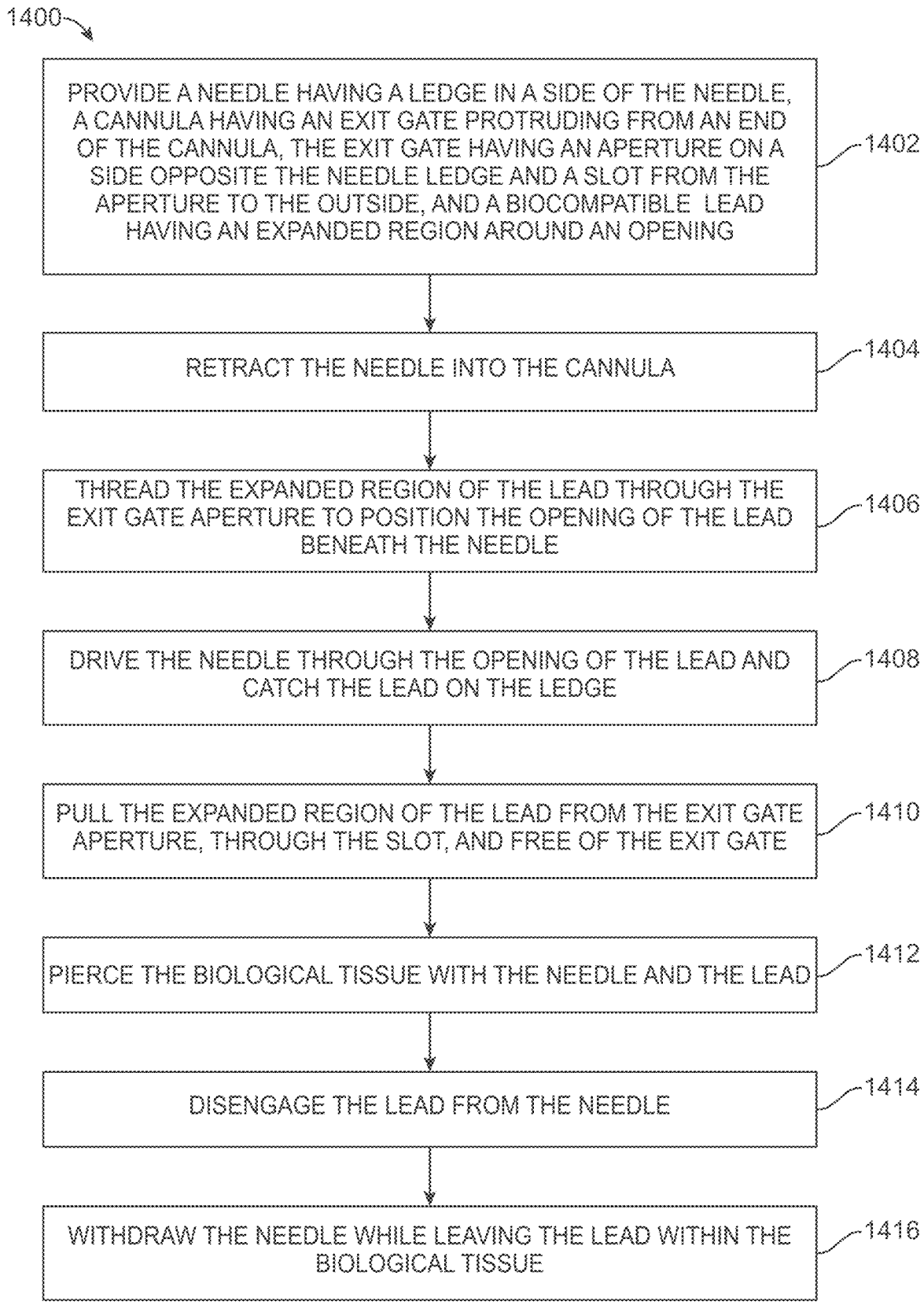
FIG. 14 is an example flowchart describing a method of engagement and implantation of a lead, according to aspects of the present disclosure.

FIG. 14 is an example flowchart describing a method 1400 of engagement and implantation of a lead, according to aspects of the present disclosure. The method 1400 may be performed by a robotic implantation system such as that depicted in FIGS. 12A-13B.

At step 1402, a needle, cannula, and biocompatible lead are provided. The needle, cannula, and lead may be configured as described above with respect to FIGS. 1A-8D. For example, the needle has a ledge in a side of the needle. The cannula has an exit gate protruding from an end of the cannula. The exit gate has an aperture on a side opposite the needle ledge and a slot from the aperture to the outside. The biocompatible lead has an expanded region around an opening.

At step 1404, the needle is retracted into the cannula. The needle may be partially extended into the cannula, such that the top region of the needle is inside the cannula and the point of the needle is extending out of the cannula (e.g., as shown in FIGS. 1A and 1B). In order to grasp the lead, the needle is retracted such that the tip of the needle is within the cannula (e.g., above the exit gate).

At step 1406, the expanded region of the lead is threaded through the exit gate aperture to position the opening of the lead beneath the needle. For example, as shown in FIG. 9C, the lead is threaded through the aperture so that the lead extends into the cannula and the opening of the lead is below the needle.

At step 1408, the needle is driven through the opening of the lead, catching the lead on the ledge. In some implementations, a robotic implantation system detects the tip of the needle and the center of the opening of the lead using one or more cameras and computer vision techniques (e.g., as described in "Computer Vision Techniques," supra). The robotic implantation system may drive cannula and needle to the opening of the lead. The needle extends down through the cannula, going through the opening of the lead. As the needle pulls down through the lead opening, the region of the lead near the opening pulls downwards, and the length of the lead is inclined at an upward angle through the aperture of the cannula. The expanded region of the lead catches on the ledge of the needle, as depicted in FIG. 1B. The needle is extended such that the combination of needle tip in loop, width of loop, and width of cannula exit gate kinematically assure that the loop will not be freed without a geometric deformation. In this configuration, the lead is held in place by the needle and cannula. The opening and expanded region of the lead are trapped in place due to the geometry of the cannula exit gate. The needle, cannula, and lead can then be positioned together, with the lead held in place, to a position for implantation. At this point, the lead is grasped and the lead can be pulled from the temporary attachment surface, as described above.

At step 1410, the expanded region of the lead is pulled from the exit gate aperture, through the slot, and free of the exit gate. Once over the insertion location, the system extends the needle. The grasping position of the needle and lead opening ensure that the needle catches on the lead, which serves to carry the lead opening, and as a result the entire lead, along with the needle as the needle is extended. As the needle extends and the lead follows, the lead width may decrease such that the lead can fall freely through the cannula exit gate. For example, when the lead has been moved to the implantation location, the needle is extended downwards, further out of the cannula. As the needle moves beyond the exit gate of the cannula, the lead, caught on the ledge of the needle, moves downwards with the needle, eventually dislodging the expanded region of the lead from the exit gate of the cannula.

At step 1412, biological tissue is pierced with the needle and the lead. The needle is driven into the biological tissue at the implantation site, inserting the lead into the biological tissue.

At step 1414, the lead is disengaged from the needle. When the needle is pulled upward, the ledge moves away from the opening and expanded region of the lead, so that the lead is no longer caught on the ledge. When the lead is inserted in the biological tissue and the needle is withdrawn at least partially, the lead is no longer trapped and can fall through the exit gate of the cannula.

At step 1416, the needle is withdrawn while leaving the lead within the biological tissue. The needle may be withdrawn back into the cannula. Alternatively, or additionally, the needle and cannula are moved together upwards. A portion of the lead remains implanted within the biological tissue (e.g., within a targeted area of brain tissue). Because the engagement between the needle and lead is unidirectional, retraction of the needle leaves the lead in the biological tissue. The leads may be implanted at a depth of about zero millimeters (mm) to thirty mm, e.g., about one mm to thirty mm, about one mm to fifteen mm, or about one mm to three mm.

In some embodiments, additional leads may be implanted by repeating steps 1402-1416. This may result in the implantation of multiple leads. For example, over 100 or over 1,000 leads can be implanted, or any other suitable number of leads such as 10 leads or 4 leads.

The systems and methods described herein may be capable of inserting about six leads per minute. For example, with 32 electrodes per lead, the system can insert up to 192 electrodes per minute. Further, the needle assembly can be replaced mid-surgery in under a minute. Accordingly, the techniques described herein enable rapid implantation of hundreds or up to tens of thousands of electrodes in biological tissue.

The leads described herein can be used for science and research experiments, neural prostheses (e.g., brain/nerve machine interfaces) and the treatment of neuronal disease (e.g., deep brain stimulation for the treatment of epilepsy, sensory recording and/or electrical stimulation for the treatment of Alzheimer's disease, sensory recording and/or electrical stimulation for the treatment of Parkinson's disease, or the like).

In some embodiments, the lead can be configured for implantation in biological tissue. Biological tissue may include, but is not limited to, the brain, muscle, liver, pancreas, spleen, kidney, bladder, intestine, heart, stomach, skin, colon and the like. Additionally, the electrode array designs may be used in connection with any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue may be ex vivo (e.g., tissue explant), or in vivo (e.g., the method is a surgical procedure performed on a patient).

Example Computer System

Figure 15:
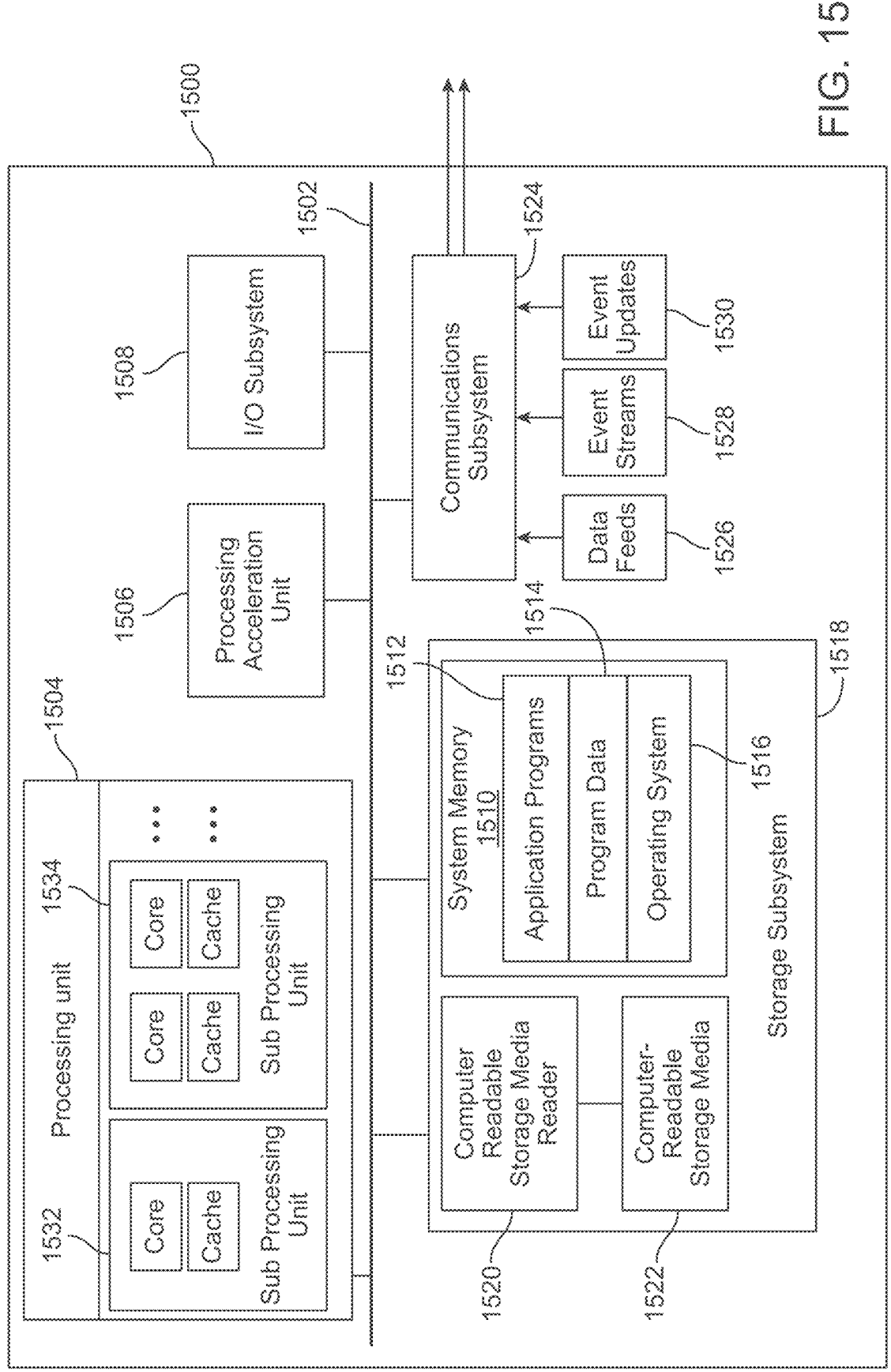
FIG. 15 illustrates an example computer system that may be used to implement certain embodiments.

FIG. 15 illustrates an example computer system 1500 that may be used to implement certain embodiments. For example, in some embodiments, computer system 1500 may be used to implement any of the systems for robotically engaging and implanting leads into biological tissue described above. As shown in FIG. 15, computer system 1500 includes various subsystems including a processing subsystem 1504 that communicates with a number of other subsystems via a bus subsystem 1502. These other subsystems may include a processing acceleration unit 1506, an I/O subsystem 1508, a storage subsystem 1518, and a communications subsystem 1524. Storage subsystem 1518 may include non-transitory computer-readable storage media including storage media 1522 and a system memory 1510.

Bus subsystem 1502 provides a mechanism for letting the various components and subsystems of computer system 1500 communicate with each other as intended. Although bus subsystem 1502 is shown schematically as a single bus, alternative embodiments of the bus subsystem may utilize multiple buses. Bus subsystem 1502 may be any of several types of bus structures including a memory bus or memory controller, a peripheral bus, a local bus using any of a variety of bus architectures, and the like. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard, and the like.

Processing subsystem 1504 controls the operation of computer system 1500 and may comprise one or more processors, application specific integrated circuits (ASICs), or field programmable gate arrays (FPGAs). The processors may include be single core or multicore processors. The processing resources of computer system 1500 can be organized into one or more processing units 1532, 1534, etc. A processing unit may include one or more processors, one or more cores from the same or different processors, a combination of cores and processors, or other combinations of cores and processors. In some embodiments, processing subsystem 1504 can include one or more special purpose co-processors such as graphics processors, digital signal processors (DSPs), or the like. In some embodiments, some or all of the processing units of processing subsystem 1504 can be implemented using customized circuits, such as application specific integrated circuits (ASICs), or field programmable gate arrays (FPGAs).

In some embodiments, the processing units in processing subsystem 1504 can execute instructions stored in system memory 1510 or on computer readable storage media 1522. In various embodiments, the processing units can execute a variety of programs or code instructions and can maintain multiple concurrently executing programs or processes. At any given time, some or all of the program code to be executed can be resident in system memory 1510 and/or on computer-readable storage media 1522 including potentially on one or more storage devices. Through suitable programming, processing subsystem 1504 can provide various functionalities described above. In instances where computer system 1500 is executing one or more virtual machines, one or more processing units may be allocated to each virtual machine.

In certain embodiments, a processing acceleration unit 1506 may optionally be provided for performing customized processing or for off-loading some of the processing performed by processing subsystem 1504 so as to accelerate the overall processing performed by computer system 1500.

I/O subsystem 1508 may include devices and mechanisms for inputting information to computer system 1500 and/or for outputting information from or via computer system 1500. In general, use of the term input device is intended to include all possible types of devices and mechanisms for inputting information to computer system 1500. User interface input devices may include, for example, a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may also include motion sensing and/or gesture recognition devices such as the Microsoft Kinect® motion sensor that enables users to control and interact with an input device, the Microsoft Xbox® 360 game controller, devices that provide an interface for receiving input using gestures and spoken commands. User interface input devices may also include eye gesture recognition devices such as the Google Glass® blink detector that detects eye activity (e.g., "blinking" while taking pictures and/or making a menu selection) from users and transforms the eye gestures as inputs to an input device (e.g., Google Glass®). Additionally, user interface input devices may include voice recognition sensing devices that enable users to interact with voice recognition systems (e.g., Siri® navigator) through voice commands.

Other examples of user interface input devices include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, and medical ultrasonography devices. User interface input devices may also include, for example, audio input devices such as MIDI keyboards, digital musical instruments and the like.

In general, use of the term output device is intended to include all possible types of devices and mechanisms for outputting information from computer system 1500 to a user or other computer. User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. For example, user interface output devices may include, without limitation, a variety of display devices that visually convey text, graphics and audio/video information such as monitors, printers, speakers, headphones, automotive navigation systems, plotters, voice output devices, and modems.

Storage subsystem 1518 provides a repository or data store for storing information and data that is used by computer system 1500. Storage subsystem 1518 provides a tangible non-transitory computer-readable storage medium for storing the basic programming and data constructs that provide the functionality of some embodiments. Storage subsystem 1518 may store software (e.g., programs, code modules, instructions) that when executed by processing subsystem 1504 provides the functionality described above. The software may be executed by one or more processing units of processing subsystem 1504. Storage subsystem 1518 may also provide a repository for storing data used in accordance with the teachings of this disclosure.

Storage subsystem 1518 may include one or more non-transitory memory devices, including volatile and non-volatile memory devices. As shown in FIG. 15, storage subsystem 1518 includes a system memory 1510 and a computer-readable storage media 1522. System memory 1510 may include a number of memories including a volatile main random access memory (RAM) for storage of instructions and data during program execution and a non-volatile read only memory (ROM) or flash memory in which fixed instructions are stored. In some implementations, a basic input/output system (BIOS), containing the basic routines that help to transfer information between elements within computer system 1500, such as during start-up, may typically be stored in the ROM. The RAM typically contains data and/or program modules that are presently being operated and executed by processing subsystem 1504. In some implementations, system memory 1510 may include multiple different types of memory, such as static random access memory (SRAM), dynamic random access memory (DRAM), and the like.

By way of example, and not limitation, as depicted in FIG. 15, system memory 1510 may load application programs 1512 that are being executed, which may include various applications such as Web browsers, mid-tier applications, relational database management systems (RDBMS), etc., program data 1514, and an operating system 1516. By way of example, operating system 1516 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, Palm® OS operating systems, and others.

Computer-readable storage media 1522 may store programming and data constructs that provide the functionality of some embodiments. Computer-readable media 1522 may provide storage of computer-readable instructions, data structures, program modules, and other data for computer system 1500. Software (programs, code modules, instructions) that, when executed by processing subsystem 1504 provides the functionality described above, may be stored in storage subsystem 1518. By way of example, computer-readable storage media 1522 may include non-volatile memory such as a hard disk drive, a magnetic disk drive, an optical disk drive such as a CD ROM, DVD, a Blu-Ray® disk, or other optical media. Computer-readable storage media 1522 may include, but is not limited to, Zip® drives, flash memory cards, universal serial bus (USB) flash drives, secure digital (SD) cards, DVD disks, digital video tape, and the like. Computer-readable storage media 1522 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs.

In certain embodiments, storage subsystem 1518 may also include a computer-readable storage media reader 1520 that can further be connected to computer-readable storage media 1522. Reader 1520 may receive and be configured to read data from a memory device such as a disk, a flash drive, etc.

In certain embodiments, computer system 1500 may support virtualization technologies, including but not limited to virtualization of processing and memory resources. For example, computer system 1500 may provide support for executing one or more virtual machines. In certain embodiments, computer system 1500 may execute a program such as a hypervisor that facilitated the configuring and managing of the virtual machines. Each virtual machine may be allocated memory, compute (e.g., processors, cores), I/O, and networking resources. Each virtual machine generally runs independently of the other virtual machines. A virtual machine typically runs its own operating system, which may be the same as or different from the operating systems executed by other virtual machines executed by computer system 1500. Accordingly, multiple operating systems may potentially be run concurrently by computer system 1500.

Communications subsystem 1524 provides an interface to other computer systems and networks. Communications subsystem 1524 serves as an interface for receiving data from and transmitting data to other systems from computer system 1500. For example, communications subsystem 1524 may enable computer system 1500 to establish a communication channel to one or more client devices via the Internet for receiving and sending information from and to the client devices. For example, the communication subsystem may be used to receive speech input from a client device and send a value to the client device in response.

Communication subsystem 1524 may support both wired and/or wireless communication protocols. For example, in certain embodiments, communications subsystem 1524 may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.XX family standards, or other mobile communication technologies, or any combination thereof), global positioning system (GPS) receiver components, and/or other components. In some embodiments communications subsystem 1524 can provide wired network connectivity (e.g., Ethernet) in addition to or instead of a wireless interface.

Communication subsystem 1524 can receive and transmit data in various forms. For example, in some embodiments, in addition to other forms, communications subsystem 1524 may receive input communications in the form of structured and/or unstructured data feeds 1526, event streams 1528, event updates 1530, and the like. For example, communications subsystem 1524 may be configured to receive (or send) data feeds 1526 in real-time from users of social media networks and/or other communication services such as Twitter® feeds, Facebook® updates, web feeds such as Rich Site Summary (RSS) feeds, and/or real-time updates from one or more third party information sources.

In certain embodiments, communications subsystem 1524 may be configured to receive data in the form of continuous data streams, which may include event streams 1528 of real-time events and/or event updates 1530, that may be continuous or unbounded in nature with no explicit end. Examples of applications that generate continuous data may include, for example, sensor data applications, financial tickers, network performance measuring tools (e.g. network monitoring and traffic management applications), clickstream analysis tools, automobile traffic monitoring, and the like.

Communications subsystem 1524 may also be configured to communicate data from computer system 1500 to other computer systems or networks. The data may be communicated in various different forms such as structured and/or unstructured data feeds 1526, event streams 1528, event updates 1530, and the like to one or more databases that may be in communication with one or more streaming data source computers coupled to computer system 1500.

Computer system 1500 can be one of various types, including a handheld portable device (e.g., an iPhone® cellular phone, an iPad® computing tablet, a PDA), a wearable device (e.g., a Google Glass® head mounted display), a personal computer, a workstation, a mainframe, a kiosk, a server rack, or any other data processing system. Due to the ever-changing nature of computers and networks, the description of computer system 1500 depicted in FIG. 15 is intended only as a specific example. Many other configurations having more or fewer components than the system depicted in FIG. 15 are possible. Based on the disclosure and teachings provided herein, a person of ordinary skill in the art will appreciate other ways and/or methods to implement the various embodiments.

It should be appreciated that the robotic system handling, coupling with, and engaging with one or more portions of a probe device can include a control system (or microprocessor controller) having one or more microprocessors/processing devices that can further be a component of the overall system. The control system can be local or remote to the robotic system, and can also include a display interface and/or operational controls configured to be handled by a user to alter the program of the robotic arm, to visualize the probe device, to visualize biological tissue into which the probe device is being inserted, and change configurations of the robotic device, and sub-portions thereof. Such processing devices can be communicatively coupled to a non-volatile memory device via a bus. The non-volatile memory device may include any type of memory device that retains stored information when powered off Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A system for implanting a device into biological tissue, comprising:
   a biocompatible lead having an opening at one end surrounded by an expanded region;
   a needle having a ledge in a side of the needle;
   a cannula into which a portion of the needle is held and can extend or retract therein; and
   an exit gate protruding from an end of the cannula, the exit gate having an aperture on a side opposite the needle ledge and sized to accept the expanded region of the lead, the exit gate having a slot from the aperture to outside,
   wherein when the expanded region of the biocompatible lead is threaded through the exit gate aperture, the needle is configured to extend through the opening of the lead and catch the lead on the ledge,
   wherein the needle is further configured to extend past the exit gate of the cannula while pulling the lead through the slot and free of the aperture.

2. The system of claim 1, further comprising: a temporary attachment surface holding the lead from which the needle and exit gate can peel the lead.

3. The system of claim 1, wherein the biocompatible lead is a first lead, the system further comprising:
   a plurality of leads including the first lead; and
   a temporary attachment surface removably coupled to the plurality of leads,
   wherein the system is configured to implant each lead of the plurality of leads.

4. The system of claim 1, wherein:
   the cannula further comprises an indentation on a second side of the cannula.

5. The system of claim 1, wherein:
the expanded region of the lead is about 1.5 times to 5 times wider than a second region of the lead.

6. The system of claim 1, wherein:
the opening of the lead has a first height; and
the expanded region of the lead has a second height greater than the first height.

7. The system of claim 6, wherein:
the second height is about 3 times to 4 times the first height.

8. The system of claim 1, further comprising:
a circuitry assembly disposed on a cranium and connected to a first end of the lead; and
an electrode for implantation in a brain of the cranium and connected to a second end of the lead.

9. The system of claim 8, the circuitry assembly further comprising:
an antenna configured to relay data.

10. The system of claim 1, further comprising:
a robotic arm configured to position and implant the needle;
a camera; and
a microprocessor controller configured to control the robotic arm and the needle using the camera in order to:
engage the lead with the needle;
pierce the biological tissue with the needle and the lead; and
withdraw the needle while leaving the lead within the biological tissue.

11. A method of implanting a device into biological tissue using a needle having a ledge in a side of the needle and a cannula having an exit gate protruding from an end of the cannula, the exit gate having an aperture on a side opposite the needle ledge and a slot from the aperture to outside, the method comprising:
retracting the needle into the cannula;
threading an expanded region of a biocompatible lead through the exit gate aperture, the expanded region surrounding an opening in the lead;
threading the expanded region of a biocompatible lead through the exit gate aperture to position the opening of the lead beneath the needle;
driving the needle through the opening of the lead and catching the lead on the ledge;
pulling the expanded region of the lead from the exit gate aperture, through the slot, and free of the exit gate;
piercing the biological tissue with the needle and the lead;
disengaging the lead from the needle; and
withdrawing the needle while leaving the lead within the biological tissue.

12. The method of claim 11, further comprising:
peeling the lead from a temporary attachment surface through motion of the needle and the cannula.

13. The method of claim 12, wherein:
multiple leads are disposed on the temporary attachment surface; and
the method further comprises peeling and implanting each of the multiple leads.

14. The method of claim 11, wherein:
a first end of the lead terminates in the opening;
a second end of the lead terminates within a circuitry assembly; and
the method further comprises disposing the circuitry assembly proximate to the biological tissue.

15. The method of claim 14, wherein:
the circuitry assembly further comprises an antenna configured to relay data.

16. The method of claim 11, wherein:
the needle is driven through the opening by controlling a robotic arm based on position information gathered using a camera.

17. The method of claim 11, wherein:
the needle engages with the lead via motion of the needle according to a single degree of freedom.

18. The method of claim 11, wherein:
the expanded region of the lead is about 1.5 times to 5 times wider than a second region of the lead.

19. The method of claim 11, wherein:
the opening of the lead has a first height; and
the expanded region of the lead has a second height about 3 times to 4 times the first height.

20. The method of claim 11, wherein:
the lead is left within the biological tissue at a depth of about one to about thirty millimeters.

* * * * *